United States Patent
Qi et al.

(10) Patent No.: US 7,303,900 B2
(45) Date of Patent: *Dec. 4, 2007

(54) METHODS FOR THE PRODUCTION OF TYROSINE, CINNAMIC ACID AND PARA-HYDROXYCINNAMIC ACID USING RECOMBINANT MICROORGANISMS

(75) Inventors: Wei Wei Qi, Broomall, PA (US); Fateme Sima Sariaslani, Wilmington, DE (US); Xiao-Song Tang, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/486,826

(22) Filed: Jul. 14, 2006

(65) Prior Publication Data

US 2006/0275881 A1    Dec. 7, 2006

Related U.S. Application Data

(62) Division of application No. 10/138,970, filed on May 3, 2002, now Pat. No. 7,105,326.

(60) Provisional application No. 60/288,701, filed on May 4, 2001.

(51) Int. Cl.
*C12P 13/22* (2006.01)
*C12N 9/02* (2006.01)
*C12N 1/20* (2006.01)
*C12N 1/00* (2006.01)
*C07H 21/04* (2006.01)

(52) U.S. Cl. ............ 435/108; 435/183; 435/189; 435/252.3; 435/254.2; 536/23.2

(58) Field of Classification Search .......... 435/108, 435/183, 189, 252.3, 254.2; 536/23.2
See application file for complete search history.

(56) References Cited

U.S. PATENT DOCUMENTS 6,368,837 B1    4/2002   Gatenby et al.
6,521,748 B2    2/2003   Tang

OTHER PUBLICATIONS

Fujisawa et al. Biochem Biophys Res Commun. Dec. 9, 2005;338(1):271-6. Epub Aug. 10, 2005.*

D. Strack, Phenolic Metabolism, Plant Biochemistry, Academic Press, 1997.

R. Benrief et al., Phytochemistry 1998, vol. 47, pp. 825-832.

Appert et al., Structural and catalytic properties of the four phenylalanine ammonia-lyase isoenzymes from parsley (petroselinum crispum Nym.), Eur. J. Biochem. vol. 225, pp. 491-499, 1994.

Havier et al., L-Phenylalanine Ammonia-Lyase Maize, Plant Physiol. vol. 48, pp. 130-136, 1971.

Hanson et al., The Biochemistry of Plants, Academic: New York, 1981, vol. 7, pp. 577-625.

Zhao et al., *Pseudomonas aeruginosa* possesses homologues of mammalian phenylalanine hydroxylase and 4α-carbinolamine dehydratase DcoH as parta of a three-component gene cluster, Proc. Natl. Sci. USA, vol. 91, 1366-1370, 1994.

Song et al., PhhR, a divergently transcribed activator of the phenylalanine hydroxylase gene cluster of *Pseudomonas aeruginosa*, Mol. Microbiol. vol. 22, pp. 497-507, 1996.

Abu-Omar et al. Book of Abstracts, 219 ACS National Meeting, San Francisco, CA, Mar. 26-30, 2000, INOR-068 Publisher: American Chemical Society, Washington, D.C.

Maladkar, Hind. Antibiot. Bull., vol. 28, 1-4, pp. 30-36, 1986.

Wang et al., Functional Characterization of A Unique Liver Gene Promoter, J. Biol. Chem. 269 (12), 9137-9146, 1994.

Hodgins DS, J. Biol. Chem. vol. 246: 2977, 1971.

Howles et al., Overespression of L-phenylalanine ammonia-lyase in transgenic tobacco plants reveals control points for flux into phenylpropanoid biosynthesis. Plant Physiology, 1996, vol. 112(4), pp. 1617-1624.

Erlandsen et al., Structural comparison of bacterial and human iron-dependent phenylalanine hydroxylases similar fold, different stability and reaction rates. J. Mol. Biol. Jul. 12, 2002, vol. 320(3), pp. 645-661.

Kyndt et al., Characterization of a bacterial tyrosine ammonia lyase, a biosynthetic enzyme for the photoactive yello protein. FEBS Lett. Feb. 13, 2002, vol. 512(1-3), pp. 240-244.

* cited by examiner

*Primary Examiner*—Tekchand Saidha
*Assistant Examiner*—Christian L. Fronda

(57) ABSTRACT

Genes encoding phenylalanine ammonia-lyase (PAL), tyrosine ammonia lyase (TAL) and phenylalanine hydroxylase (PAH) have been introduced into a host organism for the production of Para-hydroxycinnamic acid (PHCA). The introduction of these genes results in the redirection of carbon flow in the host, optimizing the flow of carbon from glucose to PHCA. The intermediates, tyrosine and cinnamic acid are also produced.

5 Claims, No Drawings

SEQUENCE LISTING

<160> NUMBER OF SEQ ID NOS: 24

<210> SEQ ID NO 1
<211> LENGTH: 894
<212> TYPE: DNA
<213> ORGANISM: C. violaceum

<400> SEQUENCE: 1

```
atgaacgacc gcgccgactt tgtggtgccc gacatcacca cccgcaagaa tgtcggactg      60
agccacgacg ccaacgactt caccttgccg cagccgttgg atcgctactc tgcggaagat     120
cacgccacct gggccacgtt gtaccagcgc caatgcaagc tgctgcccgg ccgcgcctgc     180
gacgagtttc tggaaggcct ggagcgcctg gaagtggacg ccgacagggt gccggacttc     240
aataagctca cgagaagct gatggccgcc accggctgga agatcgtcgc ggtgccgggc      300
ctgattcccg acgacgtgtt cttcgagcac ctggccaacc gccgcttccc ggtcacctgg     360
tggctgcgcg agccgcacca gctcgactac ctgcaggagc cggacgtgtt ccacgacctg     420
ttcggccacg tgccgctgct gatcaatccg gtgttcgccg attacctgga ggcctacggc     480
aagggcgggg tgaaggcgaa ggcgctgggc gcgctgccga tgctggcgcg gctgtactgg     540
tacacggtgg aattcggcct gatcaatact ccggccggca tgcgcatcta cggcgccggc     600
atcttgtcca gcaagtcgga atccatctac tgcctggaca cgccagccc caaccgcgtc      660
ggcttcgacc tgatgcgcat catgaacacg cgctaccgga tcgacacctt ccagaaaacc     720
tacttcgtca tcgacagctt caagcagctg ttcgacgcca ccgcgccgga tttcgctccg     780
ctatacttgc agctggccga cgcgcaaccg tggggcgcgc gcgacatcgc gccggacgac     840
ctggtgctga atgccggcga ccgccaagga tgggcggata ccgaagacgt ctga           894
```

<210> SEQ ID NO 2
<211> LENGTH: 297
<212> TYPE: PRT
<213> ORGANISM: C. violaceum

<400> SEQUENCE: 2

```
Met Asn Asp Arg Ala Asp Phe Val Val Pro Asp Ile Thr Thr Arg Lys
1               5                   10                  15
Asn Val Gly Leu Ser His Asp Ala Asn Asp Phe Thr Leu Pro Gln Pro
            20                  25                  30
Leu Asp Arg Tyr Ser Ala Glu Asp His Ala Thr Trp Ala Thr Leu Tyr
        35                  40                  45
Gln Arg Gln Cys Lys Leu Leu Pro Gly Arg Ala Cys Asp Glu Phe Leu
    50                  55                  60
Glu Gly Leu Glu Arg Leu Glu Val Asp Ala Asp Arg Val Pro Asp Phe
65                  70                  75                  80
Asn Lys Leu Asn Glu Lys Leu Met Ala Ala Thr Gly Trp Lys Ile Val
                85                  90                  95
Ala Val Pro Gly Leu Ile Pro Asp Asp Val Phe Phe Glu His Leu Ala
            100                 105                 110
Asn Arg Arg Phe Pro Val Thr Trp Trp Leu Arg Glu Pro His Gln Leu
        115                 120                 125
Asp Tyr Leu Gln Glu Pro Asp Val Phe His Asp Leu Phe Gly His Val
    130                 135                 140
Pro Leu Leu Ile Asn Pro Val Phe Ala Asp Tyr Leu Glu Ala Tyr Gly
145                 150                 155                 160
Lys Gly Gly Val Lys Ala Lys Ala Leu Gly Ala Leu Pro Met Leu Ala
                165                 170                 175
Arg Leu Tyr Trp Tyr Thr Val Glu Phe Gly Leu Ile Asn Thr Pro Ala
            180                 185                 190
Gly Met Arg Ile Tyr Gly Ala Gly Ile Leu Ser Ser Lys Ser Glu Ser
        195                 200                 205
```

```
Ile Tyr Cys Leu Asp Ser Ala Ser Pro Asn Arg Val Gly Phe Asp Leu
    210                 215                 220
Met Arg Ile Met Asn Thr Arg Tyr Arg Ile Asp Thr Phe Gln Lys Thr
225                 230                 235                 240
Tyr Phe Val Ile Asp Ser Phe Lys Gln Leu Phe Asp Ala Thr Ala Pro
                245                 250                 255
Asp Phe Ala Pro Leu Tyr Leu Gln Leu Ala Asp Ala Gly Pro Trp Gly
            260                 265                 270
Ala Arg Asp Ile Ala Pro Asp Asp Leu Val Leu Asn Ala Gly Asp Arg
        275                 280                 285
Gln Gly Trp Ala Asp Thr Glu Asp Val
    290                 295
```

<210> SEQ ID NO 3
<211> LENGTH: 1020
<212> TYPE: DNA
<213> ORGANISM: C. violaceum

<400> SEQUENCE: 3

```
atggcaccct cgctcgactc gatctcgcac tcgttcgcaa acggcgtcgc atccgcaaag      60
caggctgtca atggcgcctc gaccaacctc gcagtcgcag gctcgcacct gcccacaacc     120
caggtcacgc aggtcgacat cgtcgagaag atgctcgccg cgccgaccga ctcgacgctc     180
gaactcgacg gctactcgct caacctcgga gacgtcgtct cggccgcgag gaagggcagg     240
cctgtccgcg tcaaggacag cgacgagatc cgctcaaaga ttgacaaatc ggtcgagttc     300
ttgcgctcgc aactctccat gagcgtctac ggcgtcacga ctggatttgg cggatccgca     360
gacaccgca ccgaggacgc catctcgctc cagaaggctc tcctcgagca ccagctctgc     420
ggtgttctcc cttcgtcgtt cgactcgttc cgcctcggcc gcggtctcga aactcgctt     480
cccctcgagg ttgttcgcgg cgccatgaca atccgcgtca acagcttgac ccgcggccac     540
tcggctgtcc gcctcgtcgt cctcgaggcg ctcaccaact tcctcaacca cggcatcacc     600
cccatcgtcc cctccgcgg caccatctct gcgtcgggcg acctgtctcc tctctcctac     660
attgcagcgg ccatcagcgg tcacccggac agcaaggtgc acgtcgtcca cgagggcaag     720
gagaagatcc tgtacgcccg cgaggcgatg gcgctcttca acctcgagcc cgtcgtcctc     780
ggcccgaagg aaggtctcgg tctcgtcaac ggcaccgccg tctcagcatc gatggccacc     840
ctcgctctgc acgacgctca catgctctcg ctcctctcgc agtcgctcac ggccatgacg     900
gtcgaagcga tggtcggcca cgccggctcg ttccacccct tccttcacga cgtcacgcgc     960
cctcaccccga cgcagatcga agtcgcggga acatccgca agctcctcga gggaagccgc    1020
```

<210> SEQ ID NO 4
<211> LENGTH: 716
<212> TYPE: PRT
<213> ORGANISM: C. violaceum

<400> SEQUENCE: 4

```
Met Ala Pro Ser Leu Asp Ser Ile Ser His Ser Phe Ala Asn Gly Val
1               5                   10                  15
Ala Ser Ala Lys Gln Ala Val Asn Gly Ala Ser Thr Asn Leu Ala Val
            20                  25                  30
Ala Gly Ser His Leu Pro Thr Thr Gln Val Thr Gln Val Asp Ile Val
        35                  40                  45
Glu Lys Met Leu Ala Ala Pro Thr Asp Ser Thr Leu Glu Leu Asp Gly
```

-continued

```
             50                  55                  60
Tyr Ser Leu Asn Leu Gly Asp Val Val Ser Ala Ala Arg Lys Gly Arg
 65                  70                  75                  80

Pro Val Arg Val Lys Asp Ser Asp Glu Ile Arg Ser Lys Ile Asp Lys
                 85                  90                  95

Ser Val Glu Phe Leu Arg Ser Gln Leu Ser Met Ser Val Tyr Gly Val
                100                 105                 110

Thr Thr Gly Phe Gly Gly Ser Ala Asp Thr Arg Thr Glu Asp Ala Ile
                115                 120                 125

Ser Leu Gln Lys Ala Leu Leu Glu His Gln Leu Cys Gly Val Leu Pro
130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Leu Glu Ala Leu Thr
                180                 185                 190

Asn Phe Leu Asn His Gly Ile Thr Pro Ile Val Pro Leu Arg Gly Thr
                195                 200                 205

Ile Ser Ala Ser Gly Asp Leu Ser Pro Leu Ser Tyr Ile Ala Ala Ala
                210                 215                 220

Ile Ser Gly His Pro Asp Ser Lys Val His Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
                260                 265                 270

Ala Val Ser Ala Ser Met Ala Thr Leu Ala Leu His Asp Ala His Met
                275                 280                 285

Leu Ser Leu Leu Ser Gln Ser Leu Thr Ala Met Thr Val Glu Ala Met
290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Val Lys Val Lys
                340                 345                 350

Asp Asp Glu Gly Ile Leu Arg Gln Asp Arg Tyr Pro Leu Arg Thr Ser
                355                 360                 365

Pro Gln Trp Leu Gly Pro Leu Val Ser Asp Leu Ile His Ala His Ala
                370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Asn Phe Gln Ala Ala
                405                 410                 415

Ala Val Ala Asn Thr Met Glu Lys Thr Arg Leu Gly Leu Ala Gln Ile
                420                 425                 430

Gly Lys Leu Asn Phe Thr Gln Leu Thr Glu Met Leu Asn Ala Gly Met
                435                 440                 445

Asn Arg Gly Leu Pro Ser Cys Leu Ala Ala Glu Asp Pro Ser Leu Ser
450                 455                 460

Tyr His Cys Lys Gly Leu Asp Ile Ala Ala Ala Tyr Thr Ser Glu
465                 470                 475                 480
```

```
Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Ala Thr His Leu
        515                 520                 525

Tyr Cys Val Leu Gln Ala Ile Asp Leu Arg Ala Ile Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715

<210> SEQ ID NO 5
<211> LENGTH: 32
<212> TYPE: DNA
<213> ORGANISM: artificial sequence
<220> FEATURE:
<223> OTHER INFORMATION: primer

<400> SEQUENCE: 5
tccaggagcc caggatccaa cgatcgcgcc ga                                    32

<210> SEQ ID NO 6
<211> LENGTH: 28
<212> TYPE: DNA
<213> ORGANISM: artificial sequence
<220> FEATURE:
<223> OTHER INFORMATION: primer

<400> SEQUENCE: 6
ggacaagctt aatgatgcag cgacacat                                        28

<210> SEQ ID NO 7
<211> LENGTH: 22
<212> TYPE: DNA
<213> ORGANISM: artificial sequence
<220> FEATURE:
<223> OTHER INFORMATION: primer

<400> SEQUENCE: 7
```

```
gacccaggcg aattcgtaag ga                                              22

<210> SEQ ID NO 8
<211> LENGTH: 20
<212> TYPE: DNA
<213> ORGANISM: artificial sequence
<220> FEATURE:
<223> OTHER INFORMATION: primer

<400> SEQUENCE: 8
aaaaagcttg ccatcacagc                                                 20

<210> SEQ ID NO 9
<211> LENGTH: 19
<212> TYPE: DNA
<213> ORGANISM: artificial sequence
<220> FEATURE:
<223> OTHER INFORMATION: primer

<400> SEQUENCE: 9
cgttgcccgg tacctatcc                                                  19

<210> SEQ ID NO 10
<211> LENGTH: 17
<212> TYPE: DNA
<213> ORGANISM: artificial sequence
<220> FEATURE:
<223> OTHER INFORMATION: primer

<400> SEQUENCE: 10
gcggcggcga agcttct                                                    17

<210> SEQ ID NO 11
<211> LENGTH: 23
<212> TYPE: DNA
<213> ORGANISM: artificial sequence
<220> FEATURE:
<223> OTHER INFORMATION: primer

<400> SEQUENCE: 11
ggactggtac catgaccgca ctc                                             23

<210> SEQ ID NO 12
<211> LENGTH: 20
<212> TYPE: DNA
<213> ORGANISM: artificial sequence
<220> FEATURE:
<223> OTHER INFORMATION: primer

<400> SEQUENCE: 12
ccctgggcaa gcttgtagac                                                 20

<210> SEQ ID NO 13
<211> LENGTH: 25
<212> TYPE: DNA
<213> ORGANISM: artificial sequence
<220> FEATURE:
<223> OTHER INFORMATION: primer

<400> SEQUENCE: 13
accgagtggg gtaccgtcac cgtga                                           25

<210> SEQ ID NO 14
<211> LENGTH: 24
<212> TYPE: DNA
```

-continued

<213> ORGANISM: artificial sequence
<220> FEATURE:
<223> OTHER INFORMATION: primer

<400> SEQUENCE: 14
ccatcacagc aagcttaggg taac                                              24

<210> SEQ ID NO 15
<211> LENGTH: 24
<212> TYPE: DNA
<213> ORGANISM: artificial sequence
<220> FEATURE:
<223> OTHER INFORMATION: primer

<400> SEQUENCE: 15
cccacatgcg aattccaagg actc                                              24

<210> SEQ ID NO 16
<211> LENGTH: 24
<212> TYPE: DNA
<213> ORGANISM: artificial sequence
<220> FEATURE:
<223> OTHER INFORMATION: primer

<400> SEQUENCE: 16
ccatcacagc aagcttaggg taac                                              24

<210> SEQ ID NO 17
<211> LENGTH: 716
<212> TYPE: PRT
<213> ORGANISM: Rhodotorula glutinis
<220> FEATURE:
<221> NAME/KEY: MISC_FEATURE
<222> LOCATION: (126)..(126)
<223> OTHER INFORMATION: X= Gly, Ser, Ala, Thr
<220> FEATURE:
<221> NAME/KEY: MISC_FEATURE
<222> LOCATION: (138)..(138)
<223> OTHER INFORMATION: X= Leu, Met, Ile, Val, Cys
<220> FEATURE:
<221> NAME/KEY: MISC_FEATURE
<222> LOCATION: (149)..(149)
<223> OTHER INFORMATION: X=Pro, Ala, Ser, Thr, Gly
<220> FEATURE:
<221> NAME/KEY: MISC_FEATURE
<222> LOCATION: (181)..(181)
<223> OTHER INFORMATION: X=Pro, Ala, Ser, Thr, Gly
<220> FEATURE:
<221> NAME/KEY: MISC_FEATURE
<222> LOCATION: (198)..(198)
<223> OTHER INFORMATION: X=Asp, Asn, Glu, Gln
<220> FEATURE:
<221> NAME/KEY: MISC_FEATURE
<222> LOCATION: (202)..(202)
<223> OTHER INFORMATION: X=Val, Met, Leu, Cys
<220> FEATURE:
<221> NAME/KEY: MISC_FEATURE
<222> LOCATION: (235)..(235)
<223> OTHER INFORMATION: X=Ala, Gly, Ser, Pro
<220> FEATURE:
<221> NAME/KEY: MISC_FEATURE
<222> LOCATION: (502)..(502)
<223> OTHER INFORMATION: X=Gly, Ala, Ser, Thr, Pro
<220> FEATURE:
<221> NAME/KEY: MISC_FEATURE
<222> LOCATION: (540)..(540)
<223> OTHER INFORMATION: X=Thr, Ala, Ser, Pro, Gly

<400> SEQUENCE: 17

Met Ala Pro Ser Leu Asp Ser Ile Ser His Ser Phe Ala Asn Gly Val
1               5                   10                  15

-continued

```
Ala Ser Ala Lys Gln Ala Val Asn Gly Ala Ser Thr Asn Leu Ala Val
         20                  25                  30
Ala Gly Ser His Leu Pro Thr Thr Gln Val Thr Gln Val Asp Ile Val
         35                  40                  45
Glu Lys Met Leu Ala Ala Pro Thr Asp Ser Thr Leu Glu Leu Asp Gly
 50                  55                  60
Tyr Ser Leu Asn Leu Gly Asp Val Val Ser Ala Ala Arg Lys Gly Arg
 65                  70                  75                  80
Pro Val Arg Val Lys Asp Ser Asp Glu Ile Arg Ser Lys Ile Asp Lys
                 85                  90                  95
Ser Val Glu Phe Leu Arg Ser Gln Leu Ser Met Ser Val Tyr Gly Val
                100                 105                 110
Thr Thr Gly Phe Gly Gly Ser Ala Asp Thr Arg Thr Glu Xaa Ala Ile
             115                 120                 125
Ser Leu Gln Lys Ala Leu Leu Glu His Xaa Leu Cys Gly Val Leu Pro
130                 135                 140
Ser Ser Phe Asp Xaa Phe Arg Leu Gly Arg Gly Leu Glu Asn Ser Leu
145                 150                 155                 160
Pro Leu Glu Val Val Arg Gly Ala Met Thr Ile Arg Val Asn Ser Leu
                165                 170                 175
Thr Arg Gly His Xaa Ala Val Arg Leu Val Val Leu Glu Ala Leu Thr
             180                 185                 190
Asn Phe Leu Asn His Xaa Ile Thr Pro Xaa Val Pro Leu Arg Gly Thr
         195                 200                 205
Ile Ser Ala Ser Gly Asp Leu Ser Pro Leu Ser Tyr Ile Ala Ala Ala
210                 215                 220
Ile Ser Gly His Pro Asp Ser Lys Val His Xaa Val His Glu Gly Lys
225                 230                 235                 240
Glu Lys Ile Leu Tyr Ala Arg Glu Ala Met Ala Leu Phe Asn Leu Glu
                245                 250                 255
Pro Val Leu Gly Pro Lys Glu Gly Leu Gly Leu Val Asn Gly Thr
             260                 265                 270
Ala Val Ser Ala Ser Met Ala Thr Leu Ala Leu His Asp Ala His Met
             275                 280                 285
Leu Ser Leu Leu Ser Gln Ser Leu Thr Ala Met Thr Val Glu Ala Met
290                 295                 300
Val Gly His Ala Gly Ser Phe His Pro Phe Leu His Asp Val Thr Arg
305                 310                 315                 320
Pro His Pro Thr Gln Ile Glu Val Ala Gly Asn Ile Arg Lys Leu Leu
                325                 330                 335
Glu Gly Ser Arg Phe Ala Val His His Glu Glu Val Lys Val Lys
             340                 345                 350
Asp Asp Glu Gly Ile Leu Arg Gln Asp Arg Tyr Pro Leu Arg Thr Ser
             355                 360                 365
Pro Gln Trp Leu Gly Pro Leu Val Ser Asp Leu Ile His Ala His Ala
370                 375                 380
Val Leu Thr Ile Glu Ala Gly Gln Ser Thr Thr Asp Asn Pro Leu Ile
385                 390                 395                 400
Asp Val Glu Asn Lys Thr Ser His His Gly Gly Asn Phe Gln Ala Ala
                405                 410                 415
Ala Val Ala Asn Thr Met Glu Lys Thr Arg Leu Gly Leu Ala Gln Ile
             420                 425                 430
Gly Lys Leu Asn Phe Thr Gln Leu Thr Glu Met Leu Asn Ala Gly Met
```

-continued

```
                435                 440                 445
Asn Arg Gly Leu Pro Ser Cys Leu Ala Ala Glu Asp Pro Ser Leu Ser
        450                 455                 460

Tyr His Cys Lys Gly Leu Asp Ile Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Xaa Asn Ser Leu Ala Leu Ile Ser Ala Arg Arg
        500                 505                 510

Thr Thr Glu Ser Asn Asp Val Leu Ser Leu Leu Ala Thr His Leu
        515                 520                 525

Tyr Cys Val Leu Gln Ala Ile Asp Leu Arg Ala Ile Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
        580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
                660                 665                 670

Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715

<210> SEQ ID NO 18
<211> LENGTH: 716
<212> TYPE: PRT
<213> ORGANISM: Rhodotorula glutinis
<220> FEATURE:
<221> NAME/KEY: MISC_FEATURE
<222> LOCATION: (126)..(126)
<223> OTHER INFORMATION: X=Gly, Ala, Ser, Thr
<220> FEATURE:
<221> NAME/KEY: MISC_FEATURE
<222> LOCATION: (138)..(138)
<223> OTHER INFORMATION: X=Leu, Met, Ile, Val, Cys
<220> FEATURE:
<221> NAME/KEY: MISC_FEATURE
<222> LOCATION: (540)..(540)
<223> OTHER INFORMATION: X=Thr, Ala, Ser, Pro, Gly

<400> SEQUENCE: 18

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30
```

```
Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Xaa Ala Ile
            115                 120                 125

Ser Leu Gln Lys Ala Leu Leu Glu His Xaa Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
    195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
                260                 265                 270

Ala Val Ser Ala Ser Met Ala Thr Leu Ala Leu His Asp Ala His Met
            275                 280                 285

Leu Ser Leu Leu Ser Gln Ser Leu Thr Ala Met Thr Val Glu Ala Met
    290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Val Lys Val Lys
            340                 345                 350

Asp Asp Glu Gly Ile Leu Arg Gln Asp Arg Tyr Pro Leu Arg Thr Ser
            355                 360                 365

Pro Gln Trp Leu Gly Pro Leu Val Ser Asp Leu Ile His Ala His Ala
    370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Asn Phe Gln Ala Ala
                405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
    435                 440                 445

Asn Arg Gly Leu Pro Ser Cys Leu Ala Ala Glu Asp Pro Ser Leu Ser
```

```
                450             455             460
Tyr His Cys Lys Gly Leu Asp Ile Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Ala Thr His Leu
        515                 520                 525

Tyr Cys Val Leu Gln Ala Ile Asp Leu Arg Ala Xaa Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
    595                 600                 605

Val Glu Val Leu Ser Ser Thr Ser Leu Ser Leu Ala Ala Val Asn Ala
            610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
                660                 665                 670

Leu Gly Val Lys Ala Arg Arg Gly Asp Val Phe Leu Gly Lys Gln Glu
            675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715

<210> SEQ ID NO 19
<211> LENGTH: 716
<212> TYPE: PRT
<213> ORGANISM: Rhodotorula glutinis
<220> FEATURE:
<221> NAME/KEY: MISC_FEATURE
<222> LOCATION: (198)..(198)
<223> OTHER INFORMATION: X=Asp, Asn, Glu, Gln
<220> FEATURE:
<221> NAME/KEY: MISC_FEATURE
<222> LOCATION: (198)..(198)
<223> OTHER INFORMATION: Xaa=Asp, Asn, Glu, Gln
<220> FEATURE:
<221> NAME/KEY: MISC_FEATURE
<222> LOCATION: (540)..(540)
<223> OTHER INFORMATION: X=Thr, Ala, Ser, Pro, Gly

<400> SEQUENCE: 19

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45
```

-continued

```
Glu Lys Met Leu Ala Ala Pro Thr Asp Ser Thr Leu Glu Leu Asp Gly
 50                  55                  60

Tyr Ser Leu Asn Leu Gly Asp Val Val Ser Ala Ala Arg Lys Gly Arg
 65                  70                  75                  80

Pro Val Arg Val Lys Asp Ser Asp Glu Ile Arg Ser Lys Ile Asp Lys
                 85                  90                  95

Ser Val Glu Phe Leu Arg Ser Gln Leu Ser Met Ser Val Tyr Gly Val
                100                 105                 110

Thr Thr Gly Phe Gly Gly Ser Ala Asp Thr Arg Thr Glu Asp Ala Ile
                115                 120                 125

Ser Leu Gln Lys Ala Leu Leu Glu His Gln Leu Cys Gly Val Leu Pro
130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Leu Glu Ala Leu Thr
                180                 185                 190

Asn Phe Leu Asn His Xaa Ile Thr Pro Ile Val Pro Leu Arg Gly Thr
                195                 200                 205

Ile Ser Ala Ser Gly Asp Leu Ser Pro Leu Ser Tyr Ile Ala Ala Ala
210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
                260                 265                 270

Ala Val Ser Ala Ser Met Ala Thr Leu Ala Leu His Asp Ala His Met
                275                 280                 285

Leu Ser Leu Leu Ser Gln Ser Leu Thr Ala Met Thr Val Glu Ala Met
290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Val Lys Val Lys
                340                 345                 350

Asp Asp Glu Gly Ile Leu Arg Gln Asp Arg Tyr Pro Leu Arg Thr Ser
                355                 360                 365

Pro Gln Trp Leu Gly Pro Leu Val Ser Asp Leu Ile His Ala His Ala
                370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
                420                 425                 430

Gly Lys Leu Asn Phe Thr Gln Leu Thr Glu Met Leu Asn Ala Gly Met
                435                 440                 445

Asn Arg Gly Leu Pro Ser Cys Leu Ala Ala Glu Asp Pro Ser Leu Ser
450                 455                 460

Tyr His Cys Lys Gly Leu Asp Ile Ala Ala Ala Ala Tyr Thr Ser Glu
```

```
                465                 470                 475                 480
Leu Gly His Leu Ala Asn Pro Val Thr Thr His Val Gln Pro Ala Glu
                    485                 490                 495

Met Ala Asn Gln Ala Val Asn Ser Leu Ala Leu Ile Ser Ala Arg Arg
                500                 505                 510

Thr Thr Glu Ser Asn Asp Val Leu Ser Leu Leu Ala Thr His Leu
            515                 520                 525

Tyr Cys Val Leu Gln Ala Ile Asp Leu Arg Ala Xaa Glu Phe Glu Phe
        530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
                580                 585                 590

Leu Val Pro Arg Trp His Asp Ala Phe Ser Phe Ala Ala Gly Thr Val
                595                 600                 605

Val Glu Val Leu Ser Ser Thr Ser Leu Ser Leu Ala Ala Val Asn Ala
                610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                    645                 650                 655

Tyr Leu Ser Pro Arg Thr Gln Ile Leu Tyr Ala Phe Val Arg Glu Glu
                660                 665                 670

Leu Gly Val Lys Ala Arg Arg Gly Asp Val Phe Leu Gly Lys Gln Glu
                675                 680                 685

Val Thr Ile Gly Ser Asn Val Ser Lys Ile Tyr Glu Ala Ile Lys Ser
                690                 695                 700

Gly Arg Ile Asn Asn Val Leu Leu Lys Met Leu Ala
705                 710                 715

<210> SEQ ID NO 20
<211> LENGTH: 716
<212> TYPE: PRT
<213> ORGANISM: Rhodotorula glutinis
<220> FEATURE:
<221> NAME/KEY: MISC_FEATURE
<222> LOCATION: (181)..(181)
<223> OTHER INFORMATION: X=Pro, Ala, Ser, Thr, Gly
<220> FEATURE:
<221> NAME/KEY: MISC_FEATURE
<222> LOCATION: (235)..(235)
<223> OTHER INFORMATION: X=Ala, Gly, Ser, Thr, Pro
<220> FEATURE:
<221> NAME/KEY: MISC_FEATURE
<222> LOCATION: (540)..(540)
<223> OTHER INFORMATION: X=Thr, Ala, Ser, Pro, Gly
<220> FEATURE:
<221> NAME/KEY: MISC_FEATURE
<222> LOCATION: (540)..(540)
<223> OTHER INFORMATION: Xaa=Thr, Ala, Ser, Pro, Gly

<400> SEQUENCE: 20

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
                20                  25                  30

Ala Gly Ser His Leu Pro Thr Thr Gln Val Thr Gln Val Asp Ile Val
            35                  40                  45
```

```
Glu Lys Met Leu Ala Ala Pro Thr Asp Ser Thr Leu Glu Leu Asp Gly
     50                  55                  60

Tyr Ser Leu Asn Leu Gly Asp Val Val Ser Ala Arg Lys Gly Arg
 65                  70                  75                  80

Pro Val Arg Val Lys Asp Ser Asp Glu Ile Arg Ser Lys Ile Asp Lys
                 85                  90                  95

Ser Val Glu Phe Leu Arg Ser Gln Leu Ser Met Ser Val Tyr Gly Val
                100                 105                 110

Thr Thr Gly Phe Gly Gly Ser Ala Asp Thr Arg Thr Glu Asp Ala Ile
             115                 120                 125

Ser Leu Gln Lys Ala Leu Leu Glu His Gln Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Xaa Ala Val Arg Leu Val Val Leu Glu Ala Leu Thr
             180                 185                 190

Asn Phe Leu Asn His Gly Ile Thr Pro Ile Val Pro Leu Arg Gly Thr
    195                 200                 205

Ile Ser Ala Ser Gly Asp Leu Ser Pro Leu Ser Tyr Ile Ala Ala Ala
210                 215                 220

Ile Ser Gly His Pro Asp Ser Lys Val His Xaa Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
                260                 265                 270

Ala Val Ser Ala Ser Met Ala Thr Leu Ala Leu His Asp Ala His Met
             275                 280                 285

Leu Ser Leu Leu Ser Gln Ser Leu Thr Ala Met Thr Val Glu Ala Met
    290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Glu Val Lys Val Lys
             340                 345                 350

Asp Asp Glu Gly Ile Leu Arg Gln Asp Arg Tyr Pro Leu Arg Thr Ser
    355                 360                 365

Pro Gln Trp Leu Gly Pro Leu Val Ser Asp Leu Ile His Ala His Ala
    370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
             420                 425                 430

Gly Lys Leu Asn Phe Thr Gln Leu Thr Glu Met Leu Asn Ala Gly Met
    435                 440                 445

Asn Arg Gly Leu Pro Ser Cys Leu Ala Ala Glu Asp Pro Ser Leu Ser
450                 455                 460
```

```
Tyr His Cys Lys Gly Leu Asp Ile Ala Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Ala Thr His Leu
        515                 520                 525

Tyr Cys Val Leu Gln Ala Ile Asp Leu Arg Ala Xaa Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
                580                 585                 590

Leu Val Pro Arg Trp His Asp Ala Phe Ser Phe Ala Ala Gly Thr Val
            595                 600                 605

Val Glu Val Leu Ser Ser Thr Ser Leu Ser Leu Ala Ala Val Asn Ala
610                 615                 620

Trp Lys Val Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
                660                 665                 670

Leu Gly Val Lys Ala Arg Arg Gly Asp Val Phe Leu Gly Lys Gln Glu
            675                 680                 685

Val Thr Ile Gly Ser Asn Val Ser Lys Ile Tyr Glu Ala Ile Lys Ser
690                 695                 700

Gly Arg Ile Asn Asn Val Leu Leu Lys Met Leu Ala
705                 710                 715
```

<210> SEQ ID NO 21
<211> LENGTH: 716
<212> TYPE: PRT
<213> ORGANISM: Rhodotorula glutinis
<220> FEATURE:
<221> NAME/KEY: MISC_FEATURE
<222> LOCATION: (149)..(149)
<223> OTHER INFORMATION: X=Pro, Ala, Ser, Thr, Gly
<220> FEATURE:
<221> NAME/KEY: MISC_FEATURE
<222> LOCATION: (202)..(202)
<223> OTHER INFORMATION: X=Val, Met, Leu, Cys
<220> FEATURE:
<221> NAME/KEY: MISC_FEATURE
<222> LOCATION: (540)..(540)
<223> OTHER INFORMATION: X=Thr, Ala, Ser, Pro, Gly
<220> FEATURE:
<221> NAME/KEY: MISC_FEATURE
<222> LOCATION: (540)..(540)
<223> OTHER INFORMATION: Xaa=Thr, Ala, Ser, Pro, Gly

<400> SEQUENCE: 21

```
Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
```

-continued

```
                35                  40                  45
Glu Lys Met Leu Ala Ala Pro Thr Asp Ser Thr Leu Glu Leu Asp Gly
 50                  55                  60

Tyr Ser Leu Asn Leu Gly Asp Val Val Ser Ala Arg Lys Gly Arg
 65                  70                  75                  80

Pro Val Arg Val Lys Asp Ser Asp Glu Ile Arg Ser Lys Ile Asp Lys
                 85                  90                  95

Ser Val Glu Phe Leu Arg Ser Gln Leu Ser Met Ser Val Tyr Gly Val
                100                 105                 110

Thr Thr Gly Phe Gly Gly Ser Ala Asp Thr Arg Thr Glu Asp Ala Ile
                115                 120                 125

Ser Leu Gln Lys Ala Leu Leu Glu His Gln Leu Cys Gly Val Leu Pro
130                 135                 140

Ser Ser Phe Asp Xaa Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
                180                 185                 190

Asn Phe Leu Asn His Gly Ile Thr Pro Xaa Val Pro Leu Arg Gly Thr
                195                 200                 205

Ile Ser Ala Ser Gly Asp Leu Ser Pro Leu Ser Tyr Ile Ala Ala Ala
                210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
                260                 265                 270

Ala Val Ser Ala Ser Met Ala Thr Leu Ala Leu His Asp Ala His Met
                275                 280                 285

Leu Ser Leu Leu Ser Gln Ser Leu Thr Ala Met Thr Val Glu Ala Met
290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His Glu Glu Val Lys Val Lys
                340                 345                 350

Asp Asp Glu Gly Ile Leu Arg Gln Asp Arg Tyr Pro Leu Arg Thr Ser
                355                 360                 365

Pro Gln Trp Leu Gly Pro Leu Val Ser Asp Leu Ile His Ala His Ala
370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
                420                 425                 430

Gly Lys Leu Asn Phe Thr Gln Leu Thr Glu Met Leu Asn Ala Gly Met
                435                 440                 445

Asn Arg Gly Leu Pro Ser Cys Leu Ala Ala Glu Asp Pro Ser Leu Ser
450                 455                 460
```

-continued

```
Tyr His Cys Lys Gly Leu Asp Ile Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Ala Thr His Leu
        515                 520                 525

Tyr Cys Val Leu Gln Ala Ile Asp Leu Arg Ala Xaa Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715
```

<210> SEQ ID NO 22
<211> LENGTH: 716
<212> TYPE: PRT
<213> ORGANISM: Rhodotorula glutinis
<220> FEATURE:
<221> NAME/KEY: MISC_FEATURE
<222> LOCATION: (502)..(502)
<223> OTHER INFORMATION: x=Gly, Ala, Ser,Thr, Pro
<220> FEATURE:
<221> NAME/KEY: MISC_FEATURE
<222> LOCATION: (540)..(540)
<223> OTHER INFORMATION: x=Thr, Ala, Ser, Pro, Gly
<220> FEATURE:
<221> NAME/KEY: MISC_FEATURE
<222> LOCATION: (540)..(540)
<223> OTHER INFORMATION: Xaa=Thr, Ala, Ser, Pro, Gly

<400> SEQUENCE: 22

```
Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
```

```
            50                  55                  60
Tyr Ser Leu Asn Leu Gly Asp Val Ser Ala Ala Arg Lys Gly Arg
 65                  70                  75                  80

Pro Val Arg Val Lys Asp Ser Asp Glu Ile Arg Ser Lys Ile Asp Lys
                 85                  90                  95

Ser Val Glu Phe Leu Arg Ser Gln Leu Ser Met Ser Val Tyr Gly Val
                100                 105                 110

Thr Thr Gly Phe Gly Gly Ser Ala Asp Thr Arg Thr Glu Asp Ala Ile
                115                 120                 125

Ser Leu Gln Lys Ala Leu Leu Glu His Gln Leu Cys Gly Val Leu Pro
130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Leu Glu Ala Leu Thr
                180                 185                 190

Asn Phe Leu Asn His Gly Ile Thr Pro Ile Val Pro Leu Arg Gly Thr
                195                 200                 205

Ile Ser Ala Ser Gly Asp Leu Ser Pro Leu Ser Tyr Ile Ala Ala Ala
210                 215                 220

Ile Ser Gly His Pro Asp Ser Lys Val His Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
                260                 265                 270

Ala Val Ser Ala Ser Met Ala Thr Leu Ala Leu His Asp Ala His Met
                275                 280                 285

Leu Ser Leu Leu Ser Gln Ser Leu Thr Ala Met Thr Val Glu Ala Met
290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Val Lys Val Lys
                340                 345                 350

Asp Asp Glu Gly Ile Leu Arg Gln Asp Arg Tyr Pro Leu Arg Thr Ser
                355                 360                 365

Pro Gln Trp Leu Gly Pro Leu Val Ser Asp Leu Ile His Ala His Ala
370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Asn Phe Gln Ala Ala
                405                 410                 415

Ala Val Ala Asn Thr Met Glu Lys Thr Arg Leu Gly Leu Ala Gln Ile
                420                 425                 430

Gly Lys Leu Asn Phe Thr Gln Leu Thr Glu Met Leu Asn Ala Gly Met
                435                 440                 445

Asn Arg Gly Leu Pro Ser Cys Leu Ala Ala Glu Asp Pro Ser Leu Ser
450                 455                 460

Tyr His Cys Lys Gly Leu Asp Ile Ala Ala Ala Ala Tyr Thr Ser Glu
465                 470                 475                 480
```

```
Leu Gly His Leu Ala Asn Pro Val Thr Thr His Val Gln Pro Ala Glu
                485                 490                 495
Met Ala Asn Gln Ala Xaa Asn Ser Leu Ala Leu Ile Ser Ala Arg Arg
            500                 505                 510
Thr Thr Glu Ser Asn Asp Val Leu Ser Leu Leu Ala Thr His Leu
        515                 520                 525
Tyr Cys Val Leu Gln Ala Ile Asp Leu Arg Ala Xaa Glu Phe Glu Phe
    530                 535                 540
Lys Lys Gln Phe Gly Pro Ala Ile Val Ser Leu Ile Asp Gln His Phe
545                 550                 555                 560
Gly Ser Ala Met Thr Gly Ser Asn Leu Arg Asp Glu Leu Val Glu Lys
                565                 570                 575
Val Asn Lys Thr Leu Ala Lys Arg Leu Glu Gln Thr Asn Ser Tyr Asp
            580                 585                 590
Leu Val Pro Arg Trp His Asp Ala Phe Ser Phe Ala Ala Gly Thr Val
        595                 600                 605
Val Glu Val Leu Ser Ser Thr Ser Leu Ser Leu Ala Ala Val Asn Ala
    610                 615                 620
Trp Lys Val Ala Ala Ala Glu Ser Ala Ile Ser Leu Thr Arg Gln Val
625                 630                 635                 640
Arg Glu Thr Phe Trp Ser Ala Ala Ser Thr Ser Ser Pro Ala Leu Ser
                645                 650                 655
Tyr Leu Ser Pro Arg Thr Gln Ile Leu Tyr Ala Phe Val Arg Glu Glu
            660                 665                 670
Leu Gly Val Lys Ala Arg Arg Gly Asp Val Phe Leu Gly Lys Gln Glu
        675                 680                 685
Val Thr Ile Gly Ser Asn Val Ser Lys Ile Tyr Glu Ala Ile Lys Ser
    690                 695                 700
Gly Arg Ile Asn Asn Val Leu Leu Lys Met Leu Ala
705                 710                 715

<210> SEQ ID NO 23
<211> LENGTH: 2151
<212> TYPE: DNA
<213> ORGANISM: artificial sequence
<220> FEATURE:
<223> OTHER INFORMATION: mutant from Rhodotorula glutinis

<400> SEQUENCE: 23
atggcaccct cgctcgactc gatctcgcac tcgttcgcaa acggcgtcgc atccgcaaag      60
caggctgtca atggcgcctc gaccaacctc gcagtcgcag gctcgcacct gcccacaacc     120
caggtcacgc aggtcgacat cgtcgagaag atgctcgccg cgccgaccga ctcgacgctc     180
gaactcgacg gctactcgct caacctcgga gacgtcgtct cggccgcgag gaagggcagg     240
cctgtccgcg tcaaggacag cgacgagatc gctcaaaga ttgacaaatc ggtcgagttc     300
ttgcgctcgc aactctccat gagcgtctac ggcgtcacga ctggatttgg cggatccgca     360
gacacccgca ccgaggacgc catctcgctc cagaaggctc tcctcgagca ccagctctgc     420
ggtgttctcc cttcgtcgtt cgactcgttc cgcctcggcc gcggtctcga gaactcgctt     480
cccctcgagg ttgttcgcgg cgccatgaca atccgcgtca acagcttgac cgcggccac      540 tcggctgtcc gcctcgtcgt cctcgaggcg ctcaccaact tcctcaacca cggcatcacc     600
cccatcgtcc cctccgcgg caccatctct gcgtcgggcg acctctctcc tctctcctac     660
attgcagcgg ccatcagcgg tcacccggac agcaaggtgc acgtcgtcca cgagggcaag     720
```

-continued

```
gagaagatcc tgtacgcccg cgaggcgatg gcgctcttca acctcgagcc cgtcgtcctc    780
ggcccgaagg agggtctcgg tctcgtcaac ggcaccgccg tctcagcatc gatggccacc    840
ctcgctctgc acgacgcaca catgctctcg ctcctctcgc agtcgctcac ggccatgacg    900
gtcgaagcga tggtcggcca cgccggctcg ttccacccct ccttcacga cgtcacgcgc     960
cctcacccga cgcagatcga agtcgcggga acatccgca agctcctcga gggaagccgc    1020
tttgctgtcc accatgagga ggaggtcaag gtcaaggacg acgagggcat ctccgccag    1080
gaccgctacc ccttgcgcac gtctcctcag tggctcggcc cgctcgtcag cgacctcatt    1140
cacgcccacg ccgtcctcac catcgaggcc ggccagtcga cgaccgacaa ccctctcatc    1200
gacgtcgaga acaagacttc gcaccacggc ggcaatttcc aggctgccgc tgtggccaac    1260
accatggaga agactcgcct cgggctcgcc cagatcggca agctcaactt cacgcagctc    1320
accgagatgc tcaacgccgg catgaaccgc ggcctcccct cctgcctcgc ggccgaagac    1380
ccctcgctct cctaccactg caagggcctc gacatcgccc tgcggcgta cacctcggag    1440
ttgggacacc tcgccaaccc tgtgacgacg catgtccagc cggctgagat ggcgaaccag    1500
gcggtcaact cgcttgcgct catctcggct cgtcgcacga ccgagtccaa cgacgtcctt    1560
tctctcctcc tcgccaccca cctctactgc gttctccaag ccatcgactt gcgcgcgacc    1620
gagttcgagt tcaagaagca gttcggccca gccatcgtct cgctcatcga ccagcacttt    1680
ggctccgcca tgaccggctc gaacctgcgc gacgagctcg tcgagaaggt gaacaagacg    1740
ctcgccaagc gcctcgagca gaccaactcg tacgacctct cccgcgctg gcacgacgcc    1800
ttctccttcg ccgccggcac cgtcgtcgag gtcctctcgt cgacgtcgct ctcgctcgcc    1860
gccgtcaacg cctggaaggt cgccgccgcc gagtcggcca tctcgctcac ccgccaagtc    1920
cgcgagacct tctggtccgc cgcgtcgacc tcgtcgcccg cgctctcgta cctctcgccg    1980
cgcactcaga tcctctacgc cttcgtccgc gaggagcttg gcgtcaaggc ccgccgcgga    2040
gacgtcttcc tcggcaagca agaggtgacg atcggctcga acgtctccaa gatctacgag    2100
gccatcaagt cgggcaggat caacaacgtc ctcctcaaga tgctcgctta g            2151
```

<210> SEQ ID NO 24
<211> LENGTH: 716
<212> TYPE: PRT
<213> ORGANISM: artificial sequence
<220> FEATURE:
<223> OTHER INFORMATION: mutant from rhodotorula glutinis

<400> SEQUENCE: 24

```
Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
                100                 105                 110
```

-continued

```
Thr Thr Gly Phe Gly Gly Ser Ala Asp Thr Arg Thr Glu Asp Ala Ile
        115                 120                 125
Ser Leu Gln Lys Ala Leu Leu Glu His Gln Leu Cys Gly Val Leu Pro
    130                 135                 140
Ser Ser Phe Asp Ser Phe Arg Leu Gly Arg Gly Leu Glu Asn Ser Leu
145                 150                 155                 160
Pro Leu Glu Val Val Arg Gly Ala Met Thr Ile Arg Val Asn Ser Leu
                165                 170                 175
Thr Arg Gly His Ser Ala Val Arg Leu Val Val Leu Glu Ala Leu Thr
            180                 185                 190
Asn Phe Leu Asn His Gly Ile Thr Pro Ile Val Pro Leu Arg Gly Thr
        195                 200                 205
Ile Ser Ala Ser Gly Asp Leu Ser Pro Leu Ser Tyr Ile Ala Ala Ala
    210                 215                 220
Ile Ser Gly His Pro Asp Ser Lys Val His Val His Glu Gly Lys
225                 230                 235                 240
Glu Lys Ile Leu Tyr Ala Arg Glu Ala Met Ala Leu Phe Asn Leu Glu
                245                 250                 255
Pro Val Val Leu Gly Pro Lys Glu Gly Leu Gly Leu Val Asn Gly Thr
            260                 265                 270
Ala Val Ser Ala Ser Met Ala Thr Leu Ala Leu His Asp Ala His Met
        275                 280                 285
Leu Ser Leu Leu Ser Gln Ser Leu Thr Ala Met Thr Val Glu Ala Met
    290                 295                 300
Val Gly His Ala Gly Ser Phe His Pro Phe Leu His Asp Val Thr Arg
305                 310                 315                 320
Pro His Pro Thr Gln Ile Glu Val Ala Gly Asn Ile Arg Lys Leu Leu
                325                 330                 335
Glu Gly Ser Arg Phe Ala Val His His Glu Glu Glu Val Lys Val Lys
            340                 345                 350
Asp Asp Glu Gly Ile Leu Arg Gln Asp Arg Tyr Pro Leu Arg Thr Ser
        355                 360                 365
Pro Gln Trp Leu Gly Pro Leu Val Ser Asp Leu Ile His Ala His Ala
    370                 375                 380
Val Leu Thr Ile Glu Ala Gly Gln Ser Thr Thr Asp Asn Pro Leu Ile
385                 390                 395                 400
Asp Val Glu Asn Lys Thr Ser His His Gly Gly Asn Phe Gln Ala Ala
                405                 410                 415
Ala Val Ala Asn Thr Met Glu Lys Thr Arg Leu Gly Leu Ala Gln Ile
            420                 425                 430
Gly Lys Leu Asn Phe Thr Gln Leu Thr Glu Met Leu Asn Ala Gly Met
        435                 440                 445
Asn Arg Gly Leu Pro Ser Cys Leu Ala Ala Glu Asp Pro Ser Leu Ser
    450                 455                 460
Tyr His Cys Lys Gly Leu Asp Ile Ala Ala Ala Tyr Thr Ser Glu
465                 470                 475                 480
Leu Gly His Leu Ala Asn Pro Val Thr Thr His Val Gln Pro Ala Glu
                485                 490                 495
Met Ala Asn Gln Ala Val Asn Ser Leu Ala Leu Ile Ser Ala Arg Arg
            500                 505                 510
Thr Thr Glu Ser Asn Asp Val Leu Ser Leu Leu Leu Ala Thr His Leu
        515                 520                 525
```

-continued

```
Tyr Cys Val Leu Gln Ala Ile Asp Leu Arg Ala Thr Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
                660                 665                 670

Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715
```

METHODS FOR THE PRODUCTION OF TYROSINE, CINNAMIC ACID AND PARA-HYDROXYCINNAMIC ACID USING RECOMBINANT MICROORGANISMS

CROSS REFERENCE TO RELATED APPLICATIONS

This application is a divisional of U.S. patent application Ser. No. 10/138,970, filed on May 3, 2002, issued on Sep. 12, 2006 as U.S. Pat. No. 7,105,326, which claims the benefit of U.S. Provisional Application No. 60/288,701, filed May 4, 2001. These applications are incorporated herein by reference in their entirety.

FIELD OF THE INVENTION

The invention relates to the field of molecular biology and microbiology. More specifically, the invention relates to the production of tyrosine and para-hydroxycinnamic acid in a recombinant organism by the conversion of phenylalanine to tyrosine via phenylalanine hydroxylase and the subsequent conversion of tyrosine to para-hydroxycinnamic acid via tyrosine ammonium lyase.

BACKGROUND OF THE INVENTION

Production of chemicals from microorganisms has been an important application of biotechnology. Typically, the step in developing such a bio-production method may include 1) selection of a proper microorganism host, 2) elimination of metabolic pathways leading to by-products, 3) deregulation of such pathways at both enzyme activity level and the transcriptional level, and 4) overexpression of appropriate enzymes in the desired pathways. The present invention has employed combination of the steps above to redirect carbon flow from phenylalanine to tyrosine through phenylalanine hydroxylase which supplies the necessary precursor and energy for the desired biosynthesis of Para-hydroxycinnamic.

Para-hydroxycinnamic (PHCA) is a useful monomer for production of Liquid Crystal Polymers (LCP). LCP's may be used in electronic connectors and telecommunication and aerospace applications. LCP resistance to sterilizing radiation has also enabled these materials to be used in medical devices as well as chemical, and food packaging applications.

Para-hydroxycinnamic (PHCA) or p-coumarate is a known intermediate in the lignin biosynthetic pathway in plants (Plant Biochemistry, Ed. P. M. Dey, Academic Press, 1997). Methods of isolation and purification of PHCA are known (R. Benrief, et al., *Phytochemistry,* 1998, 47, 825-832; WO 972134). These methods are time consuming and cumbersome and a more facile method of production is needed for the large scale synthesis of this monomer. A fermentation route offers one possible solution.

A fermentation route to PHCA will require the engineering of several of the key enzymes involved in PHCA synthesis into an appropriate host. PHCA is a natural intermediate in the lignin biosynthetic pathway and key enzymes for synthesis may be obtained from a variety of plants. Lignin biosynthesis is initiated by the conversion of phenylalanine into cinnamate through the action of phenylalanine ammonia lyase (PAL). The second enzyme of the pathway is cinnamate-4-hydroxylase (C4H), a cytochrome P450-dependent monooxygenase (P450) which is responsible for the conversion of cinnamate to PHCA also called p-coumarate.

Thus, it is evident that one possible route to PHCA is via phenylalanine ammonia lyase (PAL) from phenylalanine. However this route also requires the presence of the second enzyme, cinnamate-4-hydroxylase, an enzyme which is rare in most microbes.

Information available indicates that PAL from some plants and micro-organisms can accept tyrosine as substrate in addition to its ability to convert phenylalanine to cinnamate. In such reactions the enzyme activity is designated tyrosine ammonia lyase (TAL). Conversion of tyrosine by TAL results in the direct formation of PHCA from tyrosine without the intermediacy of cinnamate. However, all natural PAL/TAL enzymes prefer to use phenylalanine rather than tyrosine as their substrate. The level of TAL activity is always lower than PAL activity, but the magnitude of this difference varies over a wide range. For example, the parsley enzyme has a $K_M$ for phenylalanine of 15-25 µM and for tyrosine 2.0-8.0 mM with turnover numbers 22/sec and 0.3/sec respectively (Appert et al., *Eur. J. Biochem.* 225:491 (1994)). In contrast, the maize enzyme has a $K_M$ for phenylalanine only fifteen times higher than for tyrosine, and turnover numbers about ten-fold higher (Havir et al., *Plant Physiol.* 48:130 (1971)). The exception to this rule, is the yeast, *Rhodosporidium*, in which a ratio of TAL catalytic activity to PAL catalytic activity is approximately 0.58 (Hanson and Havir in *The Biochemistry of Plants*; Academic: New York, 1981; Vol. 7, pp 577-625). Thus an alternate pathway to PHCA, might involve the direct conversion of tyrosine to PHCA via TAL, assuming an abundant source of tyrosine. Tyrosine is however, generally in low supply in most microorganisims, whereas phenylalanine is abundant. A method to convert phenylalanine to tyrosine would facilitate the pathway to PHCA through TAL.

Phenylalanine hydroxylase (PAH) systems appear to be infrequent in prokaryotes. Phenylalanine hydroxylase has been reported in a few species belonging to the α division of the class *Proteobacteria* and in *Pseudomonas aeruginosa* in, the γ division (Zhao et al., *Proc. Natl. Acad. Sci. USA.* 91: 1366 (1994)). Of these, *Pseudomonas aeruginosa* is the best characterized at the molecular-genetic level (Song et al. *Mol. Microbiol.* 22:497-507 (1996) and Zhao et al., *Proc. Natl. Acad. Sci. USA.* 91: 1366 (1994)). *Pseudomonas aeruginosa* possesses a multi-gene operon that includes phenylalanine hydroxylase which is homologous with mammalian phenylalanine hydroxylase, tryptophan hydroxylase, and tyrosine hydroxylase (Zhao et al., *Proc. Natl. Acad. Sci. USA.* 91: 1366 (1994)). The bacterial Phenylalanine hydroxylase from *Pseudomonas aeruginosa* and *Chromobacterium violaceum* has been cloned, expressed, purified, and fully characterized (Abu-Omar et al. Book of Abstracts, 219 ACS National Meeting, San Francisco, Calif., Mar. 26-30, (2000) INOR-068 Publisher: American Chemical Society, Washington, D.C.)). Moreover, the presence of PAH in *Streptomyces aureofaciens* has been demonstrated (Maladkar, Hind. *Antibiot. Bull.,* 28: 1-4, 30-6 (1986)).

The enzymatic conversion of phenylalanine to tyrosine is known in eukaryotes. Human phenylalanine hydroxylase is specifically expressed in the liver to convert L-phenylalanine to L-tyrosine (Wang et al. *J. Biol. Chem.* 269 (12): 9137-46 (1994)). Deficiency of the PAH enzyme causes classic phenylketonurea, a common genetic disorder.

The literature is silent as to the conversion of glucose to para-hydroxycinnamic acid via re-directing the carbon flow from phenylalanine to tyrosine through phenylalanine hydroxylase maximizing the concentration of tyrosine in the cells to allow for the use of the TAL pathway for conversion of glucose to PHCA.

The problem to be solved here is to develop an industrially suitable method for production of tyrosine and para-hydroxycinnamic acid using genetically engineered microorganisms.

Applicants have solved the stated problem by engineering several recombinant microorganisms comprising at least one gene encoding a phenylalanine hydroxylase activity and at least one gene encoding a phenylalanine and tyrosine ammonium lyase activity for the production of tyrosine and para-hydroxycinnamic acid from fermentable carbon substrates.

SUMMARY OF THE INVENTION

The invention provides a method for the production of para-hydroxycinnamic acid comprising:
  a) providing a recombinant organism comprising:
   i) at least one gene encoding a tyrosine ammonium lyase activity; and
   ii) at least one gene encoding a phenylalanine hydroxylase activity;
  b) growing said recombinant organism in the presence of a fermentable carbon substrate whereby para-hydroxycinnamic is produced.

Additionally the invention provides a method for the production of tyrosine comprising:
  a) providing a recombinant organism comprising at least one gene encoding a phenylalanine hydroxylase activity; and
  b) growing said recombinant organism in the presence of a fermentable carbon substrate whereby tyrosine is produced.

In another embodiment the invention provides recombinant hosts comprising:
  i) at least one gene encoding a tyrosine ammonium lyase activity; and
  ii) at least one gene encoding a phenylalanine hydroxylase activity.

BRIEF DESCRIPTION OF THE SEQUENCE DESCRIPTIONS AND BIOLOGICAL DEPOSITS

The invention can be more fully understood from the following detailed description and the accompanying sequence descriptions which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence encoding the C. violaceum Phenylalanine hydroxylase enzyme.

SEQ ID NO:2 is the deduced amino acid sequence of the C. violaceum Phenylalanine hydroxlase enzyme encoded by the nucleotide sequence of SEQ ID NO:1

SEQ ID NO:3 is the nucleotide sequence encoding the wildtype R. glutinis PAL enzyme.

SEQ ID NO:4 is the deduced amino acid sequence encoded by the nucleotide sequence encoding the wildtype R. glutinis PAL enzyme.

SEQ ID NO:5 and SEQ ID NO:6 are primers used for the isolation of the PAH gene of the Chromobacterium violaceum.

SEQ ID NOs:7-16 are primers designed and used for amplifying the PAH operon and its components in the E. coil hosts:

SEQ ID NOs:17-22 are mutant TAL proteins having amino acid substitutions within the wildtype R. glutinis PAL/TAL amino acid.

SEQ ID NO:23 is the nucleotide sequence encoding the mutant or modified R. glutinis PAL enzyme having enhanced TAL activity.

SEQ ID NO:24 is the deduced amino acid sequence encoded by the nucleotide sequence encoding the mutant R. glutinis PAL enzyme having enhanced TAL activity.

Applicants made the following biological deposits under the terms of the Budapest Treaty on the International Recognition of the Deposit of Micro-organisms for the Purposes of Patent Procedure:

| Depositor Identification Reference | International Depository Designation | Date of Deposit |
|---|---|---|
| P. aeruginosa containing the modified PAL (SEQ ID NO: 23) and the C. violaceum PAH (SEQ ID NO: 1) | PTA 3349 | May 2, 2001 |

DETAILED DESCRIPTION OF THE INVENTION

The present invention describes biological methods for the production of tyrosine, and PHCA. Furthermore, the present invention relates to the microorganisms which are genetically modified to increase carbon flow into the production of PHCA. Specifically, the present invention provides a method of producing tyrosine and PHCA in a phenylalanine producing microorganism using the phenylalanine hydroxylase gene of lactobacilli or bacilli to first convert phenylalanine to tyrosine.

In this disclosure, a number of terms and abbreviations are used. The following definitions are provided.

"Phenylalanine ammonia-lyase" is abbreviated PAL.

"Tyrosine ammonia lyase" is abbreviated TAL.

"Para-hydroxycinnamic acid" is abbreviated PHCA.

"Cinnamate 4-hydroxylase" is abbreviated C4H.

"Phenylalanine hydroxylase" is abbreviated PAH

"Phenylalanine 4-monooxygenase" is abbreviated phh A.

"4-alpha-carbinolamine dehydratase" is abbreviated phh B.

"Aromatic aminotransferase" is abbreviated phh C.

"4-alpha-carbinolamine dehydratase and aromatic aminotransferase" is abbreviated phh BC.

"Phenylalanine 4-monooxygenase and 4alpha-carbinolamine dehydratase" is abbreviated as phhAB Phenylalanine 4-monooxygenase and aromatic aminotransferase is abbreviated as phhAC The term "Full operon" refers to a DNA fragment comprising phh A, phh B and phhC genes The term "TAL activity" or "TAL enzyme" refers to the ability of a protein to catalyze the direct conversion of tyrosine to Para-hydroxycinnamic acid (PHCA).

The term "PAL activity" or "PAL enzyme" refers to the ability of a protein to catalyze the conversion of phenylalanine to cinnamic acid.

The term "PAL/TAL activity" or "PAL/TAL enzyme" refers to a protein which contains both PAL and TAL activity. Such a protein has at least some specificity for both tyrosine and phenylalanine as an enzymatic substrate.

The term "modified PAL/TAL" or "mutant PAL/TAL" refers to a protein which has been derived from a wild type PAL enzyme which has greater TAL activity than PAL activity. As such, a modified PAL/TAL protein has a greater substrate specificity for tyrosine than for phenylalanine.

The term "PAH" activity" or "PAH enzyme" refers to a protein which catalyzes the conversion of phenylalanine to tyrosine.

As used herein the terms "cinnamic acid" and "cinnamate" are used interchangeably.

The term "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

"Gene" refers to a nucleic acid fragment that expresses a specific protein, including regulatory sequences preceding (5' non-coding sequences) and following (3' non-coding sequences) the coding sequence. "Native gene" or "wild type gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

"Coding sequence" refers to a DNA sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic-acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product-along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "amino acid" will refer to the basic chemical structural unit of a protein or polypeptide. The following abbreviations will be used herein to identify specific amino acids:

| Amino Acid | Three-Letter Abbreviation | One-Letter Abbreviation |
| --- | --- | --- |
| Alanine | Ala | A |
| Arginine | Arg | R |

-continued

| Amino Acid | Three-Letter Abbreviation | One-Letter Abbreviation |
|---|---|---|
| Asparagine | Asn | N |
| Aspartic acid | Asp | D |
| Asparagine or aspartic acid | Asx | B |
| Cysteine | Cys | C |
| Glutamine | Gln | Q |
| Glutamine acid | Glu | E |
| Glutamine or glutamic acid | Glx | Z |
| Glycine | Gly | G |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "chemically equivalent amino acid" will refer to an amino acid that may be substituted for another in a given protein without altering the chemical or functional nature of that protein. For example, it is well known in the art that alterations in a gene which result in the production of a chemically equivalent amino acid at a given site, but do not effect the functional properties of the encoded protein are common. For the purposes of the present invention substitutions are defined as exchanges within one of the following five groups:
  1. Small aliphatic, nonpolar or slightly polar residues: Ala, Ser, Thr (Pro, Gly);
  2. Polar, negatively charged residues and their amides: Asp, Asn, Glu, Gln;
  3. Polar, positively charged residues: His, Arg, Lys;
  4. Large aliphatic, nonpolar residues: Met, Leu, Ile, Val (Cys); and
  5. Large aromatic residues: Phe, Tyr, Trp.

Thus, alanine, a hydrophobic amino acid, may be substituted by another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. Additionally, in many cases, alterations of the N-terminal and C-terminal portions of the protein molecule would also not be expected to alter the activity of the protein.

Standard recombinant DNA and molecular cloning techniques used here are well known in the art and are described by Sambrook, J., Fritsch, E. F. and Maniatis, T. *Molecular Cloning: A Laboratory Manual*, 2$^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments With Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

The present invention describes a method for the production of tyrosine as well as p-hydroxycinnamic acid in a recombinant microbial organism that produces phenylalanine. For the production of tyrosine the recombinant microorganism will contain a heterologus gene encoding a Phenylalanine hydroxylase (PAH) activity. For the production of p-hydroxycinnamic acid the recombinant organism will additionally contain a gene encoding a tyrosine ammonium lyase (TAL) activity. The relevant pathway is illustrated below:

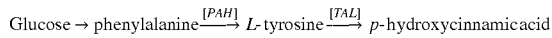

$$\text{Glucose} \rightarrow \text{phenylalanine} \xrightarrow{[PAH]} L\text{-tyrosine} \xrightarrow{[TAL]} p\text{-hydroxycinnamic acid}$$

The present method relies on a source of phenylalanine in the recombinant host. Phenylalanine may either be supplied exogenously or produced endogenously by the cell.

The invention is useful for the biological production of PHCA which may be used as a monomer for production of Liquid Crystal Polymers (LCP). LCP's may be used in electronic connectors and telecommunication and aerospace applications. LCP resistance to sterilizing radiation has also enabled these materials to be used in medical devices as well as chemical, and food packaging applications.

Additionally the invention provides a new method for the production of tyrosine, an amino acid used widely in industrial microbiology and in pharmaceutical synthetic methods.

Genes

The key enzymatic activities used in the present invention are encoded by a number of genes known in the art. The principal enzymes are phenylalanine hydroxylase (PAH) and tyrosine ammonium lyase (TAL).

Phenylalanine Hydroxylase (PAH) and Tyrosine Ammonium Lyase (TAL)

The invention provides a recombinant organism having PAH activity that is useful for the conversion of phenylalanine to tyrosine. This enzyme is well known in the art and has been reported in *Proteobacteria* (Zhao et al., In *Proc. Natl. Acad. Sci. USA*. 91: 1366 (1994)). For example *Pseudomonas aeruginosa* possesses a multi-gene operon that includes phenylalanine hydroxylase which is homologous with mammalian phenylalanine hydroxylase, tryptophan hydroxylase, and tyrosine hydroxylase (Zhao et al., In *Proc. Natl. Acad. Sci. USA*. 91: 1366 (1994

The enzymatic conversion of phenylalanine to tyrosine is known in eukaryotes. Human Phenylalanine hydroxylase is specifically expressed in the liver to convert L-phenylalanine to L-tyrosine (Wang et al. *J. Biol. Chem.* 269 (12): 9137-46 (1994)).

Although any gene encoding a PAH activity will be useful, and genes isolated from *Proteobacteria* will be particularly suitable, in the present invention it is preferred that genes encoding the PAH be isolated from *Chromobacterium violaceum* as set forth in SEQ ID NO:1.

In nature genes encoding phenylalanine ammonia-lyase are known to convert phenylalanine to cinnamate which may then be converted to Para-hydroxycinnamic acid via a p-450/p-450 reductase enzyme system. In many instances the phenylalanine-ammonia-lyase has dual substrate specificity acting on phenylalanine principally, but also having some affinity for tyrosine. For example, the PAL enzyme isolated from parsley (Appert et al., *Eur. J. Biochem.* 225: 491 (1994)) and corn ((Havir et al., *Plant Physiol.* 48:130 (1971)) both demonstrate the ability to use tyrosine as a substrate. Similarly, the PAL enzyme isolated from *Rhodosporidium* (Hodgins D S, *J. Biol. Chem.* 246:2977 (1971)) also may use tyrosine as a substrate. Such enzymes will be referred to herein as PAL/TAL enzymes or activities. Where it is desired to create a recombinant organism expressing a wild type gene encoding PAL/TAL activity, genes isolated from maize, wheat, parsley, *Rhizoctonia solani*, *Rhodosporidium*, *Sporobolomyces pararoseus* and *Rhodosporidium* may be used as discussed in Hanson and Havir, *The Biochemistry of Plants*; Academic: New York, 1981; Vol. 7, pp 577-625, where the genes from *Rhodosporidium* are preferred and the gene as set forth in SEQ ID NO:3 is most preferred.

In some instances it will be possible to increase the substrate specificity of the PAL/TAL enzyme via various forms of mutagenesis and protein engineering. A variety of approaches may be used for the mutagenesis of the PAL/TAL enzyme. Suitable approaches for mutagenesis include error-prone PCR (Leung et al., *Techniques*, 1:11-15 (1989) and Zhou et al., *Nucleic Acids Res.* 19:6052-6052 (1991) and Spee et al., *Nucleic Acids Res.* 21:777-778 (1993)) and in vivo mutagenesis. Protein engineering may be accomplished by the method commonly known as "gene shuffling" (U.S. Pat. Nos. 5,605,793; 5,811,238; 5,830,721; and 5,837,458), or by rationale design based on three-dimensional structure and classical protein chemistry. Applicants have used a variety of these methods to determine which amino acid alterations within the classical *Rhodosporidium* PAL/TAL enzyme (SEQ ID NO:4) will give enhanced substrate specificity for tyrosine. These mutants, the altered amino acid residues, and the TAL/PAL activity are summarized below.

| Strain | Mutations | TAL/PAL ratio |
|---|---|---|
| Wild Type PAL | None | 0.5 |
| EP18Km-6 (mutant PAL | CTG(Leu215) to CTC(Leu) | 1.7 |
|  | GAA(Glu264) to GAG(Glu) |  |
|  | GCT(Ala286) to GCA(Ala) |  |
|  | ATC(Ile540) to ACC(Thr) |  |
| RM120-1 | GAC(Asp126) to GGC(Gly) | 7.2 |
|  | CAG(Gln138) to CTG(Leu) |  |
|  | CTG(Leu215) to CTC(Leu) |  |
|  | GAA(Glu264) to GAG(Glu) |  |
|  | GCT(Ala286) to GCA(Ala) |  |
|  | ATC(Ile540) to ACC(Thr) |  |
| RM120-2 | TTG(Leu176) to CTG(Leu) | 2.1 |
|  | GGC(Gly198) to CAC(Asp) |  |
|  | CTG(Leu215) to CTC(Leu) |  |
|  | GAA(Glu264) to GAG(Glu) |  |
|  | GCT(Ala286) to GCA(Ala) |  |
|  | ATC(Ile540) to ACC(Thr) |  |
| RM120-4 | TCG(Ser181) to CCG(Pro) | 2.0 |
|  | GTC(Val235) to GCC(Ala) |  |
|  | CTG(Leu215) to CTC(Leu) |  |
|  | GAA(Glu264) to GAG(Glu) |  |
|  | GCT(Ala286) to GCA(Ala) |  |
|  | ATC(Ile540) to ACC(Thr) |  |
| RM120-7 | TCG(Ser149) to CCG(Pro) | 0.8 |
|  | ATC(Ile202) to GTC(Val) |  |
|  | CTG(Leu215) to CTC(Leu) |  |
|  | GAA(Glu264) to GAG(Glu) |  |
|  | GCT(Ala286) to GCA(Ala) |  |
|  | ATC(Ile540) to ACC(Thr) |  |
| RM492-1 | GTC(Val502) to GGC(Gly) | 2.0 |
|  | CTG(Leu215) to CTC(Leu) |  |
|  | GAA(Glu264) to GAG(Glu) |  |
|  | GCT(Ala286) to GCA(Ala) |  |
|  | ATC(Ile540) to ACC(Thr) |  |

It will be appreciated that the invention encompasses, not only the specific mutations described above, but also those that allow for the substitution of chemically equivalent amino acids. So for example where a substitution of an amino acid with the aliphatic, nonpolar amino acid alanine is made, it will be expected that the same site may be substituted with the chemically equivalent amino acid serine. Thus the invention provides mutant TAL proteins having the following amino acid substitutions within the wildtype PAL/TAL amino acid sequence (SEQ ID NO:4):

| Sequence ID No. | Position | WT Amino Acid | Possible Amino Acids |
|---|---|---|---|
| 17 | 126 | Asp | Gly, Ala, Ser, Thr |
|  | 138 | Gln | Leu, Met, Ile, Val, Cys |
|  | 149 | Ser | Pro, Ala, Ser, Thr, Gly |
|  | 181 | Ser | Pro, Ala, Ser, Thr, Gly |
|  | 198 | Gly | Asp, Asn, Glu, Gln |
|  | 202 | Ile | Val, Met, Leu, Cys |
|  | 235 | Val | Ala, Gly, Ser, Thr, Pro |
|  | 502 | Val | Gly, Ala, Ser, Thr, Pro |
|  | 540 | Ile | Thr, Ala, Ser, Pro, Gly |
| 18 | 126 | Asp | Gly, Ala, Ser, Thr |
|  | 138 | Gln | Leu, Met, Ile, Val, Cys |
|  | 540 | Ile | Thr, Ala, Ser, Pro, Gly |
| 19 | 198 | Gly | Asp, Asn, Glu, Gln |
|  | 540 | Ile | Thr, Ala, Ser, Pro, Gly |
| 20 | 181 | Ser | Pro, Ala, Ser, Thr, Gly |
|  | 235 | Val | Ala, Gly, Ser, Thr, Pro |
|  | 540 | Ile | Thr, Ala, Ser, Pro, Gly |
| 21 | 149 | Ser | Pro, Ala, Ser, Thr, Gly |
|  | 202 | Ile | Val, Met, Leu, Cys |
|  | 540 | Ile | Thr, Ala, Ser, Pro, Gly |
| 22 | 502 | Val | Gly, Ala, Ser, Thr, Pro |
|  | 540 | Ile | Thr, Ala, Ser, Pro, Gly |

In addition to the rationale modifications recited above, mutations may be generated randomly. In the instant case a modified PAL enzyme was created from the wildtype *R. glutinis* PAL which had enhanced TAL activity. This mutation was created by error prone PCR and is set forth in SEQ ID NO:23, encoding a protein as set forth in SEQ ID NO:24.

It will be appreciated that the present invention is not limited to any specific sequence encoding either Phenylalanine hydroxylase or Tyrosine ammonia lyase activities but rather may be supplemented by genes having similar activities known in the art and obtainable by routine sequence dependant protocols. Examples of sequence-dependent protocols include, but are not limited to, methods of nucleic acid hybridization, and methods of DNA and RNA amplification as exemplified by various uses of nucleic acid amplification technologies (e.g., polymerase chain reaction (PCR), ligase chain reaction (LCR)).

For example, genes encoding homologs of anyone of the mentioned activities (TAL, or PAH) could be isolated directly by using all or a portion of the known sequences as DNA hybridization probes to screen libraries from any desired plant, fungi, yeast, or bacteria using methodology well known to those skilled in the art. Specific oligonucleotide probes based upon the literature nucleic acid sequences can be designed and synthesized by methods known in the art (Maniatis, supra). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency. By these and other protocols a variety of genes encoding the Tyrosine ammonia lyase and phenylalanine hydroxylase activities may be isolated.

Microbial Hosts

The production organisms of the present invention will include any organism capable of expressing the genes required for PHCA or tyrosine production. Typically the production organism will be restricted to microorganisms.

Microorganisms useful in the present invention for the production of PHCA and tyrosine may include, but are not limited to bacteria, such as the enteric bacteria (*Escherichia*, and *Salmonella* for example) as well as *Bacillus, Acinetobacter, Streptomyces, Methylobacter, Rhodococcus* and *Pseudomona; Cyanobacteria*, such as *Rhodobacter* and *Synechocystis*; yeasts, such as *Saccharomyces, Zygosaccharomyces, Kluyveromyces, Candida, Hansenula, Debaryomyces, Mucor, Pichia* and *Torulopsis*; and filamentous fungi such as *Aspergillus* and *Arthrobotrys*, and algae for example. The PAL/TAL and PAH genes of the present invention may be produced in these and other microbial hosts to prepare large, commercially useful amounts of PHCA and tyrosine.

Microbial expression systems and expression vectors containing regulatory sequences that direct high level expression of foreign proteins are well known to those skilled in the art. Any of these could be used to construct chimeric genes for production of PHCA. These chimeric genes could then be introduced into appropriate microorganisms via transformation to allow for expression of high level of the enzymes.

Vectors or cassettes useful for the transformation of suitable microbial host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the relevant genes in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, trp, $IP_L$, $IP_R$, T7, tac, and trc (useful for expression in *Escherichia coli*).

Termination control regions may also be derived from various genes native to the preferred hosts. Optionally, a termination site may be unnecessary, however, it is most preferred if included.

Where commercial production of PHCA or tyrosine is desired a variety of fermentation methodologies may be applied. For example, large scale production may be effected by both batch or continuous fermentation.

A classical batch fermentation is a closed system where the composition of the media is set at the beginning of the fermentation and not subject to artificial alterations during the fermentation. Thus, at the beginning of the fermentation the medium is inoculated with the desired microorganism or microorganisms and fermentation is permitted to occur adding nothing to the system. Typically, however, the concentration of the carbon source in a "batch" fermentation is limited and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in the log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the medium. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, T. D.; *Biotechnology: A Textbook of Industrial Microbiology*, 2nd ed.; Sinauer Associates: Sunderland, Mass., 1989; or Deshpande, M. V. *Appl. Biochem. Biotechnol.* 36:227, (1992), herein incorporated by reference.

Commercial production of PHCA or tyrosine may also be accomplished with continuous fermentation. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in their log phase of growth.

Continuous fermentation allows for modulation of any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by the medium turbidity, is kept constant. Continuous systems strive to maintain steady state growth conditions and thus the cell loss due to the medium removal must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

Production of PHCA or tyrosine will require suitable carbon substrates. Suitable substrates may include but are not limited to monosaccharides such as glucose, raffinose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, formaldehyde, formate or methanol for which metabolic conversion into key biochemical intermediates has been demonstrated.

Description of the Preferred Embodiments.

The PAH gene of the *Chromobacterium violaceum* (SEQ ID NO:1) was cloned and expressed in both *Pseudomonas* aeruginosa and DH5α E. coli. Production of tyrosine, cinnamate, and PHCA by Pseudomonas aeruginosa strains containing the PAH gene of Chromobacterium violaceum (SEQ ID NO:1) was demonstrated. Pseudomonas aeruginosa was demonstrated to lack p-450/p-450 reductase enzyme system needed to convert cinnamate to Para-hydroxycinnamic acid and thus all the Para-hydroxycinnamic acid produced in these experiments resulted from the re-direction of carbon flow through phenylalanine to tyrosine and then to Para-hydroxycinnamic acid. The production of cinnamate is likely a byproduct of the phenylalanine ammonia-lyase activity retained by the PAL/TAL enzyme.

In a particular application of the methods of the instant invention, it has been found that transformants of P. aeruginosa containing the PAH operon for conversion of phenylalanine to tyrosine with the modified PAL/TAL gene (SEQ ID NO:23) had an increased flow of carbon to tyrosine and an increased amount PHCA produced.

In a preferred embodiment, incorporation of C. violaceum PAH gene in combination with the expression of the endogenous P. aeruginosa PAH operon and the modified PAL/TAL resulted in increased amount of tyrosine and PHCA produced.

In another embodiment, P. aeruginosa PAH was cloned and expressed in the phenylalanine over-producing Escherichia coli and E. coli auxotrphic strain.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. Molecular Cloning: A Laboratory Manual; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in Biotechnology: A Textbook of Industrial Microbiology, Second Edition, Sinauer-Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "sec" means second(s), "min" means minute(s), "h" means hour(s), "psi" means pounds per square inch, "nm" means nanometers, "d" means day(s), "µL" means microliter, "mL" means milliliters, "L" means liters, "mm" means millimeters, "nm" means nanometers, "mM" means millimolar, "M" means molar, "mmol" means millimole(s), "µmole" mean micromole", "g" means gram, "µg" means microgram and "ng" means nanogram, "U" means units, "mU" means milliunits and "U mg$^{-1}$" means units per mg.

Description of Strains:

Pseudomonas aeruginosa ATCC 15691 was used throughout as a control. Strain ATCC 15691 contains a native PAH operon, but lacks any PAL or TAL enzymatic functions and lacks the necessary p-450/p-450 reductase enzyme system to convert cinnamate to Para-hydroxycinnamic acid. Pseudomonas aeruginosa ATCC 15691 was also transformed with the native PAL/TAL from R. glutinis giving it the ability to convert phenylalanine to cinnamate. Additionally the Pseudomonas aeruginosa ATCC15691 was transformed with a mutant PAL/TAL enzyme [SEQ ID NO:23] (based on the R. glutinis wildtype sequence, SEQ ID NO:4) having enhanced substrate specificity for tyrosine. Additionally a Pseudomonas aeruginosa ATCC 15691 transformant was created containing a gene encoding the PAH from C. violaceum (SEQ ID NO:1) and a gene encoding the wildtype PAL from R. glutinis (SEQ ID NO:3). In similar fashion Pseudomonas aeruginosa ATCC 15691 was transformed with a gene encoding mutant PAL/TAL from R. glutinis [SEQ ID NO:23] having enhanced TAL activity and a gene encoding the PAH from C. violaceum (SEQ ID NO:1). In addition to Pseudomonas aeruginosa ATCC 15691, E. coli phenylalanine over producers were transformed with mutant and wildtype PAL/TAL genes, and PAH genes from C. violaceum.

The strains of the present invention are labeled in the following examples as follows:
Control=Pseudomonas aeruginosa (ATCC 15691)
TAL=Pseudomonas aeruginosa (ATCC15691) containing the modified PAL/TAL (SEQ ID NO:23) from R. glutinis
PAH/TAL=Pseudomonas aeruginosa (ATCC 15691) containing the modified PAL/TAL (SEQ ID NO:23) from R. glutinis and the
PAH (SEQ ID NO:1) from C. violaceum Electroporation of Pseudomonas aeruginosa (ATCC 15691):

Samples of glycerol stocks of P. aeruginosa were spread onto agarose plates without any antibiotics and incubated overnight at 37° C. when colonies were at least 1.0 mm in diameter and dense. Cells (~1.0-3.0 mg) were harvested from the plates and transferred to a tube using a sterile inoculating loop. Three generous swipes across a plate were usually satisfactory for obtaining the required samples. Collected cells were then resuspended, washed once in sterile water and resuspended in water (500 µl).

Plasmid DNA (~50 ng, plasmids described below) was added to the tubes containing the cells. The DNA/cell suspensions were then transferred to pre-chilled electroporation cuvettes (0.1 cm, Bio-Rad, Hercules, Calif.) and the cuvettes were kept on ice. Each sample was electrically pulsed at 18 kV/cm in a Gene Pulser (Bio-Rad) (25 µF, 200 om). SOC medium (1.0 ml) was added to each cuvette immediately after pulsing. The cell mixtures were then transferred to tubes and left on the shaker (1.0 hr at 37° C., 220 rpm). Samples (100 µl) of each transformation reaction were then pipetted onto separate LB plates and incubated overnight at 37° C.

Enzyme Activity Assay

The PAL or TAL activity of the purified enzymes was measured using a spectrophotometer according to Abell et al., "Phenylalanine Ammonia-lyase from Yeast *Rhodotorula glutinis,*" *Methods Enzymol.* 142:242-248 (1987). The spectrophotometric assay for PAL determination was initiated by the addition of the enzyme to a solution containing 1.0 mM L-phenylalanine and 50 mM Tris-HCl (pH 8.5). The reaction was then followed by monitoring the absorbance of the product, cinnamic acid, at 290 nm using a molar extinction coefficient of 9000 $cm^{-1}$. The assay was run over a 5 min period using an amount of enzyme that produced absorbance changes in the range of 0.0075 to 0.018/min. One unit of activity indicated deamination of 1.0 µmol of phenylalanine to cinnamic acid per minute. The TAL activity was similarly measured using tyrosine in the reaction solution. The absorbance of the para-hydroxycinnamic acid produced was followed at 315 nm and the activity was determined using an extinction coefficient of 10,000 $cm^{-1}$ for PHCA. One unit of activity indicated deamination of 1.0 µmol of tyrosine to para-hydroxycinnamic acid per minute.

SDS Gel Electrophoresis

The 8-25% native PhastGels were run with 4.0 µg of protein per lane and stained with Coomassie blue. Pharmacia High Molecular Weight (HMW) markers and grade I PAL from Sigma were used as standards.

Sample Preparation for HPLC Analysis

An HPLC assay was developed for measuring the levels of cinnamic acid and PHCA formed by the whole cells. In a typical assay, following centrifugation of a culture grown in the medium of choice, 20-1000 µL of the supernatant was acidified with phosphoric acid, filtered through a 0.2 or 0.45 micron filter and analyzed by the HPLC to determine the concentration of PHCA and cinnamic acid in the growth medium. Alternatively, following centrifugation, the cells were resuspended in 100 mM Tris-HCl (pH 8.5) containing 1.0 mM tyrosine or 1.0 mM phenylalanine and incubated at room temperature for 1.0-16 h. A filtered aliquot (20-1000 µL) of this suspension was then analyzed.

The HPLC Method:

A Hewlett Packard 1090M HPLC system with an auto sampler and a diode array UV/vis detector was used with a reverse-phase Zorbax SB-C8 column (4.6 mm×250 mm) supplied by MAC-MOD Analytical Inc. Flow rate of 1.0 mL per min, at column temperature of 40° C. was carried out. The UV detector was set to monitor the eluant at 250, 230, 270, 290 and 310 nm wavelengths.

Solvents/Gradients:

| Time (min) | Solvent A Methanol | Solvent B 0.2% TFA |
|---|---|---|
| 0.0 | 10% | 90% |
| 0.1 | 10% | 90% |
| 9.0 | 35% | 65% |
| 9.1 | 50% | 50% |
| 14.0 | 50% | 50% |
| 18.0 | 0% | 0% |
| 21.0 | 0% | 0% |

Retention time (RT) of related metabolites using the HPLC system described above are summarized below.

| Compounds (1.0 mM) | RT (min) |
|---|---|
| 1. tyrosine | 6.7 |
| 2. phenylalanine | 9.4 |
| 3. 4-hydroxybenzoic acid (PHBA) | 11.6 |
| 4. 3,4-dihydroxycinnamate (caffeic acid) | 12.5 |
| 5. 3-(4-hydroxyphenyl)propionate | 13.3 |
| 6. 4-hydroxyphenylpyruvate | 13.6 |
| 7. 4-hydroxyacetaphenone | 14.0 |
| 8. 4-hydroxycinnamic acid (PHCA) | 14.2 |
| 9. 2-hydroxycinnamic acid (OHCA) | 15.3 |
| 10. benzoic acid | 15.5 |
| 11. coumarin | 16.0 |
| 12. cinnamyl alcohol | 17.3 |
| 13. phenylpyruvate | 18.1 |
| 14. cinnamic acid | 18.3 |

MONO Q Buffer:

The buffer used for these analyses was a 50 mM potassium phosphate, pH 7.0, as the starting buffer followed by a 400 mM potassium phosphate buffer, pH 7.2 as eluent for the Mono-Q column.

EXAMPLE 1

Cloning and Expression of *Chromobacterium violaceum* Phyenylalanine Hydroxylase in Microorganisms Phenylalanine Hydroxylase for *Chromobacterium violaceum* DNA Amplification and Cloning In these studies the PAH gene of the *Chromobacterium violaceum* (SEQ ID NO:1) was cloned into both *Pseudomonas aeruginosa* (ATCC15691) and DH5α *E. coli*. Two oligonucleotide primers, 5'-TCCAGGAGCCCAGGATCCAACGATCGCGCCGA-3'[SEQ ID NO:5], (designated CVPH168), and 5'-GGACAAGCTTAATGATGCAGCGACACAT-3'[SEQ ID NO:6], (designated CVPH1170) were synthesized based on the deoxynucleotide sequences flanking the coding region of the *C. violaceum* phenylalanine hydroxylase gene described previously (A. Onishi, L. J. Liotta, S. J. Benkovic; Cloning and Expression of *Chromobacterium violaceum* phenylalanine hydroxylase in *Escherichia coli* and comparison of amino acid sequence with mammalian aromatic amino acid hydroylase *J. Biol. Chem.* 266:18454-18459 (1991)). Restriction endonuclease sites (BamHI or HindIII, underlined sequences of the above primers) were designed at the 5'-prime end of each primer to facilitate cloning. *C. violaceum* genomic DNA was isolated and purified with Qiagen Kit and the DNA amplification carried out. The amplification reaction mixture (100 µl) contained 1.0 mg of the genomic DNA template, 100 pmol each of the two primers, 2.5 units of Taq DNA polymerase (Qiagen) in 10 mM Tris-HCl, (pH 8.8), 0.2 mM each of the four dNTPs, 50 mM KCl, 1.5 mM MgCl2, and 0.01% bovine serum albumin. Thirty PCR cycles (94 C, 0.5 min; 55 C, 0.5 min and 72 C, 2.0 min) were performed. The correctly amplified DNA fragments (based on the fragment size) were cloned into a TA vector (Invitrogen, Carlsbad, Calif.) and submitted for sequence analysis. Several clones containing the gene were thus obtained.

Gene Expression and Protein Purification:

To express the cloned phenylalanine hydroxlyase gene, the amplified DNA fragments of interest were purified using a GeneClean II Kit (Bio 101, Inc, Carlsbad, Calif.), digested with endonuclease BamHI and HindIII (Promega, Madison, Wis.) and cloned into the BamHI and HindIII sites in plasmid vectors such as pET24a (Novogen, Madison, Wis.), pQE30 (Qiagen) and pTrc99A (Pharmacia, Piscataway, N.J.). The following designations were used for the vectors prepared: pETDW (PET24a vector containing PAH gene from *C. violaceum* (SEQ ID NO:1)). PQSW-PAH1170 (pQE30 vector containing the same gene) and pTrc-PAH (pTrc99a containing the PAH gene). The *Pseudomonas* and *E. coli* strains transformed electroporationally with the expression vectors were grown at 37° C. in LB medium containing either 25 mg/ml of kanamycin for vpESW-PAH1170 or 100 mg/ml of ampicillin for both pQSE-PAH1170 and pTrc-PAH in the absence or presence of isopropyl-beta-D-thiogalactoside (IPTG). Expression of the recombinant phenylalanine-hydroxylase was analyzed by SDS-polyacrylamide gel electrophoresis. Purification of phenylalanine hydroxylase to homogeneity was accomplished by passing the cell suspensions in 50 mM acetate buffer pH 6.0 containing 1 μg/ml of leupeptin and pepstatin A through the French Pressure cell (×2) at 18,000 psi. Protease inhibitor, PMSF, was then added to the extract to a final concentration of 0.5 mM. Cell debris and inclusion bodies were removed by centrifugation at 38,000×g for 20 min. The supernatant was then used as the cell free extract.

Anion exchange was carried out on a 20 mm×165 mm, 50 μm HQ column at a flow of 30 ml/min. The starting buffer (buffer A) was 50 mM sodium acetate pH 6.0 containing 20 mM NaCl and the eluting buffer (buffer B) was 50 mM sodium acetate pH 6.0 containing 500 mM NaCl. The column was equilibrated and washed with buffer A after sample injection. A gradient was run from 100% of buffer A to 100% of buffer B over ten column volumes. The column was washed with buffer B and then re-equilibrated with buffer A. Protein was monitored at 280 nm and 10 ml fractions were collected after two column volumes of the gradient. All of the crude extract was used in one run on the column. Fractions containing PAH activity were pooled, and concentrated by Centricom-10 ultrafiltration. The purified enzyme was stored at −70° C. after being frozen in liquid nitrogen. The purity of the phenylalanine hydroxylase was judged by inspection of Coomassie Blue stained SDS polyacrylamide gels following electrophoresis of the samples.

TABLE 1

Purification of PAH from recombinant *E. coli*

| Purification Step | Total protein Concentration Yield (mg) | Total enzyme activity (U)[a] | Specific act. (U mg$^{-1}$) | (fold)(%) |
|---|---|---|---|---|
| Crude Extract 1 | 100 | 206 | 3481.5 | 16.93 |
| Anion Exchange 51 | 47 | 1770.0 | 37.76 | 2.23 |
| Gel Filtration 33 | 32 | 1162.8 | 35.82 | 2.12 |

[a]One unit corresponds to 1 μmol of tyrosine produced per min.

Determination of the Phenylalanine Hydroxylase Enzyme Activity and Protein Concentration:

The phenylalanine-dependent DMPH4 dehydrogenation activity was measured by monitoring tyrosine production spectrophotometrically. The assays were performed by the addition of the enzyme solution (1.0-10 ml) to a 1.0 ml solution containing L-phenylalanine (1.0 mM, 10 ml of a 100 mM solution); Dithiotreitol (DTT, 6.0 mM, 6.0 ml of a 1.0 M solution); Fe(NH$_4$)$_2$(SO$_4$)$_2$ (1.0 mM, 10 ml of a 100 mM solution), 6,7-dimtheyltetrahydropterin (DMPH4)(120 mM, 10 ml of a 12 mM solution)and HEPES buffer (960 ml of 100 mM, pH 7.4). The reaction was initiated by the addition of phenylalanine to the above mixture and followed by monitoring the increase at 275 nm due to the formation of the product, tyrosine. The assay was run for several minutes using an amount of enzyme that produced a change of absorbance around 0.01/min. Activities were determined using a molar extinction coefficient of 1700 cm$^{-1}$. One unit of enzyme activity will produce 1.0 umol of tyrosine per minute. The concentration of the enzyme in solutions was routinely determined by the BCA protein assay (Bio-Rad Laboratories, Hercules, Calif.).

In Vivo Production of Tyrosine:

Assays for in vivo tyrosine production were conducted by HPLC methods. The microorganisms containing the phenylalanine hydroxylase gene were inoculated into the LB medium with corresponding antibiotics in the presence or absence of cofactor DMPH4 and/or FeSO4. Cells were left on the shaker at 37° C. overnight. The cultures were then washed (×3) with M9 medium containing 2% glucose and resuspended in the same medium. Samples (1.0 ml) were taken at specified time intervals and prepared and analyzed by HPLC.

EXAMPLE 2

Production of Tyrosine, Cinnamate and PHCA by *Pseudomonas aeruginosa* Strains Containing the Phenylalanine Hydroxylase Gene of *Chromobacterium violaceum*

This example describes expression of the phenylalanine hydroxylase from *C. violaceum* in *Pseudomonas aeruginosa*.

In order to confirm the source of Para-hydroxycinnamic acid produced in of *P. aeruginosa* (ATCC 15691) it was first necessary to confirm that of *P. aeruginosa* (ATCC 15691) did not have the enzymatic machinery to produce Para-hydroxycinnamic acid from cinnamate. To confirm this the following study was done.

A single colony was picked up from the LB agar plate and inoculated into 4.0 ml of the LB medium. The cultures were left on the shaker (30° C., 225 rpm) overnight. Then 200 ul of the culture was transferred into 150.0 ml of fresh LB medium and the cultures were left on the shaker (30° C., 225 rpm) overnight. Cells were then centrifuged and washed twice with the M9 medium containing 2% glucose. The cell pellet was then re-suspended into either the M9 medium, M9 medium containing 2% glucose, LB medium and LB medium containing 2% glucose and the OD at 600 nm was adjusted to 0.2. Either pHCA or cinnamate (1.0 mM) were added to the cultures which were then left on the shaker (30° C.). Cultures that did not receive either PHCA or cinnamate were used as Controls. Samples (1.0 ml) were taken from the of cultures at 24 hours and 48 hours for HPLC analysis. Results of the analyses are summarized below (Table 2) and indicate that *P. aeruginosa* could not produce PHCA from cinnamate and was not consumed in substantial amounts.

TABLE 2

Consumption of PHCA and Cinnamate by Wild Type *P. aeruginosa*
(1.0 mM PHCA or 1.0 mM Cinnamate added)

| Medium | 24 hours | 48 hours |
|---|---|---|
| | PHCA conc. (mM) | |
| M9 medium with glucose | 0.90 | 0.87 |
| LB medium with glucose | 0.95 | 0.98 |
| M9 medium | 0.95 | 0.91 |
| LB medium | 1.00 | 0.92 |
| | Cinnamate concentration. (mM) | |
| M9 medium with glucose | 0.87 | 0.85 |
| LB medium with glucose | 0.88 | 0.87 |
| M9 medium | 0.80 | 0.70 |
| LB medium | 0.95 | 0.84 |

The recombinant strains used in this study were prepared by electroporation of *P. aeruginosa* (ATCC 15691) with the expression vectors pE-PAL (containing the native PAL/TAL from *Rhodotorula glutinis* with Ampicillin selection marker) and pJ-PAH (containing PAH from *Chromobacterium violaceum* (SEQ ID NO:1) with Kanamycin selection marker). The double selection plate contained the LB medium plus Carbenicillin (175 µg/ml) and Kanamycin, (150 µg/ml). Single colonies were picked up from the selective plates and inoculated into tubes containing the LB medium (10 ml) with antibiotics. Cultures were left on the shaker overnight (37° C. and 225 rpm). They were then centrifuged, washed once with LB medium and resuspended in 10 ml of the same medium. Isopropyl beta-D-thiogalactoside (IPTG, 10 µl of a 1.0 M stock solution) was added to the cultures (final concentration 1.0 mM) and left on the shaker, (37° C., 225 rpm, 24 hr). Samples (1.0 ml) were taken after 24 hours of induction with IPTG and prepared for HPLC analysis to determine the concentrations of tyrosine, cinnamate and PHCA in them. Results of HPLC analysis are summarized in Table 3. The control cells (native *P. aeruginosa* containing the *Pseudomonas* PAH operon), and the PAL and TAL transformants did not produce any tyrosine following growth on the LB medium. However, *Pseudomonas* transformants containing the PAH from *C. violaceum* [SEQ ID NO:1] (in addition to their native PAH) and those transformants containing either the PAH/PAL or PAH/TAL produced 233.5, 13.6 and 23.5 M of tyrosine respectively under these experimental conditions. Analysis for cinnamic acid production by various strains indicated production of very low levels (1.45 and 12.2 M respectively) of cinnamate by both the native *P. aeruginosa* strain and the cells containing the PAH from *C. violaceum* [SEQ ID NO:1]. However cells containing either PAL or TAL showed much higher levels of cinnamate production (322.3 and 220.8 M respectively). Cells that contained *C. violaceum* PAH in addition to either PAL or TAL showed formation of lower amounts-(204.8 and 109.5 m respectively) of cinnamate compared to those containing only PAL or TAL. Similarly only small amounts of PHCA (0.46 and 0.37 M respectively) was formed by the Control and the PAH containing cells while much higher levels of PHCA (188.9 and 285.1 M respectively) were observed with cells containing PAL and TAL or the combination of PAH/PAL and PAH/TAL (155.6 and 207.5 m respectively). These results clearly underline the effect of the PAH enzyme in diverting the flow of Carbon from phenylalanine to tyrosine as attested by observation of tyrosine in *Pseudomonas* recombinant strains containing the *C. violaceum* gene in addition to their native PAH operon. The fact that somewhat lower levels of PHCA was formed by transformants containing both PAH and PAL or TAL could reflect the rate limiting role of PAH in these cells.

TABLE 3

Tyrosine, Cinnamate and PHCA Production
by *P. aeruginosa* Transformants

| Transformants | Tyrosine (µM) | PHCA (µM) | Cinnamic Acid (µM) |
|---|---|---|---|
| Control | 0 | 0.46 | 1.45 |
| PAL | 0 | 188.9 | 322.3 |
| TAL | 0 | 285.1 | 220.8 |
| PAH | 233.5 | 0.37 | 12.2 |
| PAH/PAL | 13.6 | 155.6 | 204.8 |
| PAH/TAL | 23.5 | 207.5 | 109.5 |

EXAMPLE 3

Production of Tyrosine, Cinnamic Acid and PHCA
by Recombinant *Pseudomonas aeruginosa* Strains
Following Growth in M9 Plus Glucose Production
of Tyrosine, Cinnamic Acid and PHCA by
Recombinant *Pseudomonas aeruginosa* Strains:

Recombinant strains used in this study were those described in Example 1. Experimental procedure was similar to that of Example 1 with the exception that in this example, cells were grown on the defined M9 medium and then glucose was added as the sole source of carbon and the samples were taken for analysis after 6 hours instead of 24 hours. The change in the growth medium from LB (Example 2) to the defined M9 plus glucose (Example 3) resulted in a significant reduction in the cell mass produced and therefore the values obtained for the concentration of tyrosine, cinnamate and PHCA produced are significantly lower than those obtained in Example 1.

The results obtained indicated that the Control cells (although they already contained the native PAH operon) could not produce tyrosine from glucose. When these cells were transformed with modified PAL/TAL (SEQ ID NO:23), tyrosine (95.54 M) was observed in the 6 hour samples. However, these cells did not produce any cinnamate and/or PHCA. When TAL was incorporated into the *Pseudomonas* cells negligible amounts of tyrosine (3.44 M) were detected. Cinnamate and PHCA (18.49 M and 13.59 M respectively) were detected in these cultures. The transformants containing both PAH and TAL produced the highest levels of tyrosine, cinnamate and PHCA (97.24 M, 23.44 M, and 19.19 M respectively). Production of cinnamate by cells containing TAL and/or PAH/TAL confirms the results discussed in Example 1 that over-expression of the PAH in the *Pseudomonas* is required to allow for tyrosine production in the medium and that the TAL still contains some PAL activity.

TABLE 4

Tyrosine, PHCA, and Cinnamic Acid Production from
Glucose by *P. aeruginosa* Transformants

| | Product Production (µM) | | |
|---|---|---|---|
| Transformants | Tyrosine | PHCA | Cinnamic Acid |
| Control | 0 | 0 | 0 |
| PAH | 95.54 | 0 | 0 |

TABLE 4-continued

Tyrosine, PHCA, and Cinnamic Acid Production from
Glucose by *P. aeruginosa* Transformants

| Transformants | Product Production (μM) | | |
|---|---|---|---|
| | Tyrosine | PHCA | Cinnamic Acid |
| TAL | 3.44 | 13.59 | 18.49 |
| PAH/TAL | 97.24 | 19.19 | 23.44 |

EXAMPLE 4

Tyrosine and PHCA Production by *P. aeruginosa* TAL Transformants with or without Phenylalanine Addition The *P. aeruginosa* contains the PAH operon for conversion of phenylalanine to tyrosine. Transformants of this strain were prepared with the modified PAL/TAL gene (SEQ ID NO:23) in order to study the effect of the *P. aeruginosa*'s PAH operon on increasing the flow of carbon to tyrosine and therefore increasing the amount of PHCA produced. Transformants were grown in the LB medium and were then divided into two groups. To one group, phenylalanine (0.1 mM) was added while the other group did not receive any additional phenylalanine. Samples were taken after 6.0 hours and as can be seen in the Table 5. The level of tyrosine detected in the medium increased from ~23 M in control uninduced cells to ~66 M by the IPTG induced transformants without additional phenylalanine to ~350 M by the induced transformants which had received additional phenylalanine. Control cells did not produce any PHCA while ~10 and 13.0 M of PHCA was detected in the cultures without and with phenylalanine addition respectively.

TABLE 5

Tyrosine and PHCA Production by *P. aeruginosam* PAL/TAL Transformants with or without Phenylalanine Addition

| Sample | Product Production (μM) | |
|---|---|---|
| | Tyrosine | PHCA |
| Control (uninduced) | 22.59 | 0 |
| No Phenylalanine Addition | 65.55 | 9.77 |
| 0.1 mM Phenylalanine Addition | 350.61 | 13.72 |

EXAMPLE 5

Tyrosine and PHCA Production by *P. aeruginosa* PAH Transformants with or without Phenylalanine Addition Experiments were performed using the *P. aeruginosa* transformed with the *C. violaceum* PAH (SEQ ID NO:1) to investigate their ability to produce tyrosine (Table 6). Cells were grown in the LB medium and were then divided into two groups. To one group, phenylalanine (0.1 mM) was added while the other group did not receive any additional phenylalanine. Samples were taken after 6.0 hours and as can be seen in the Table 6. The level of tyrosine detected in the medium increased from ~69.0 M in control uninduced cells to ~174 M by the IPTG induced transformants without additional phenylalanine to ~424 M by the induced transformants which had received additional phenylalanine. Due to the absence of PAL/TAL gene, none of the cells in this study produced any PHCA during the course of the study (Table 6).

TABLE 6

Tyrosine and PHCA Production by *P. aeruginosa* PAH Transformants with or without Phenylalanine Addition

| Sample | Product Production (μM) | |
|---|---|---|
| | Tyrosine | PHCA |
| Control (uninduced) | 68.58 | 0 |
| No Phenylalanine Addition | 174.22 | 0 |
| 0.1 mM Phenylalanine Addition | 424.33 | 0 |

EXAMPLE 6

Tyrosine and PHCA Production by *P. aeruginosa* PAH/TAL Transformants with or without Phenylalanine Addition In order to study the combined effect of incorporation of the *C. violaceum* PAH, in addition to the endogenous *P. aeruginosa* PAH operon, and the modified PAL/TAL (SEQ ID NO:23) on the level of tyrosine and the PHCA formed the following experiment was performed. The *P. aeruginosa* was transformed with both *C. violaceum* PAH gene (SEQ ID NO:1) and the modified PAL/TAL gene (SEQ ID NO:23). Cells were grown in the LB medium in the presence and absence of additional phenylalanine. Table 7 summarizes the results obtained. Levels of both PHCA and tyrosine increased in induced cells that had received additional phenylalanine. When levels of tyrosine and PHCA were compared it was obvious that the rate limiting step in complete conversion of phenylalanine to PHCA via the TAL route was the PAL/TAL enzyme.

EXAMPLE 8

Cinnamate and PHCA Production by *P. aeruginosa* TAL Transformants with or without Phenylalanine Addition The *P. aeruginosa* cells used in Example 5 which contained the modified PAL/TAL gene (SEQ ID NO:23) were grown in the M9 plus glucose and Mg$^{+2}$ and the levels of cinnamate and PHCA formed were measured. In all cells tested, the levels of cinnamate were higher than those observed for PHCA attesting to the presence of higher PAL than TAL activity in the modified enzyme (Table 9).

TABLE 9

Cinnamate and PHCA Production by *P. aeruginosa* TAL Transformants with or without Phenylalanine Addition

| Sample | Product Production (μM) | |
|---|---|---|
| | Cinnamate | PHCA |
| Control (uninduced) | 86.46 | 40.93 |
| No Phenylalanine Addition | 132.39 | 129.73 |
| 0.1 mM Phenylalanine Addition | 916.55 | 206.21 |

EXAMPLE 9

The *P. aeruginosa* cells used in Example 6 which contained both *C. violaceum* PAH gene (SEQ ID NO:1) and the modified PAL/TAL gene (SEQ ID NO:23) were used in this experiment. They were grown in the M9 plus glucose and $Mg^{+2}$ and the levels of cinnamate and PHCA were measured after 24 hours. In all cases, higher levels of cinnamate compared to PHCA were produced (Table 10).

TABLE 10

Cinnamate and PHCA Production by *P. aeruginosa* PAH/TAL Transformants with or without Phenylalanine Addition

| Sample | Product Production (μM) | |
|---|---|---|
| | Cinnamate | PHCA |
| Control (uninduced) | 15.82 | 10.34 |
| No Phenylalanine Addition | 61.54 | 122.97 |
| 0.1 mM Phenylalanine Addition | 520.59 | 177.12 |

EXAMPLE 10

Cloning and Expression of the *Pseudomonas aeruginosa* Phenylalanine Hydroxylase (PAH)Operon in the Phenylalanine Over-producing *Escherichia Coli* Phenylalanine Hydroxylase (PAH) of *Pseudomonas aeruginosa*: DNA Amplification and Cloning:

The primers listed in the Table 11 were designed for use in incorporation of the PAH operon from *P. aeruginosa* into the phenylalanine over-producing *E. coli* strain (ATCC 31884) and the *E. coli* tyrosine auxotrophic strain (AT2741). The following primers of the *P. aeruginosa* operon designed and used for amplifying the PAH operon and its components in the *E. coli* hosts:

TABLE 11

| Name | Sequence | *Re Site | Gene |
|---|---|---|---|
| Primer3' SEQ ID NO:7 | 5'-GACCCAGGCGAATTCGTAA GGA-3' | EcoRI | Full operon |
| Primer2' SEQ ID NO:8 | 5'-AAAAAGCTTGCCATCACAG C-3' | HindIII | |
| PhhA-5' SEQ ID NO:9 | 5'-CGTTGCCCGGTACCTATC C-3' | KpnI | Phh A |
| phhA-3' SEQ ID NO:10 | 5'-GCGGCGGCGAAGCTTCT-3' | HindIII | |
| PhhB-5' SEQ ID NO:11 | 5'-GGACTGGTACCATGACCGC ACTC-3' | KpnI | Phh B |
| phhB-3' SEQ ID NO:12 | 5'-CCCTGGGCAAGCTTGTAGA C-3' | HindIII | |
| PhhC-5' SEQ ID NO:13 | 5'-ACCGAGTGGGGTACCGTCA CCGTGA-3' | KpnI | Phh C |
| PhhC-3' SEQ ID NO:14 | 5'-CCATCACAGCAAGCTTAGG GTAAC-3' | HindIII | |
| PAHm1-5' SEQ ID NO:15 | 5'-CCCACATGCGAATTCCAAG GACTC-3' | EcoRI | PhhB/ PhhC |
| PAHm4-3' SEQ ID NO:16 | 5'-CCATCACAGCAAGCTTAGG GTAAC-3' | HindIII | |

*Restriction site is abbreviated Re site.

The oligonucleotide primers (Table 11) were synthesized based on the deoxynucleotide-sequences flanking the coding region of the *P. aeruginosa* phenylalanine hydroxylase gene operon described previously (Zhao G, Xia T, Song J and Jensen RA (1994) *Proc. Natl. Acad. Sci., USA* 91: 1366-1370). Restriction endonuclease sites (underlined sequences of the above primers of Example 1, SEQ ID NOs:5 and 6) were designed at the 5'-primer end of each primer to facilitate cloning. The *P. aeruginosa* genomic DNA was isolated and purified with Qiagen Kit and the DNA amplification was carried out. The amplification reaction mixture (100 μl) contained 1.0 mg of the genomic DNA template, 100 pmol each of the two primers, 2.5 units of Taq DNA polymerase(Qiagen) in 10 mM Tris-HCl, (pH 8.8), 0.2 mM each of the four dNTPs, 50 mM KCl, 1.5 mM MgCl2, and 0.01% bovine serum albumin. Thirty PCR cycles (94° C., 0.5 min; 55° C., 0.5 min and 72° C., 2.0 min) were performed. The correctly amplified DNA fragments (based on the fragment size) were cloned into a TA vector (Invitrogen, Carlsbad, Calif.) and submitted for sequence analysis. Several clones containing the gene were thus obtained.

Gene Expression and Protein Purification

To express the cloned phenylalanine hydroxlyase gene operon and its individual components, the amplified DNA fragments of interest were purified using a GeneClean II Kit (Bio 101, Inc, Carlsbad, Calif.), digested with endonucleases (Promega, Madison, Wis.) and cloned into the restriction endonuclease sites in plasmid vectors such as pD100 (ATCC87222), pKSM715 (ATCC87161) and pTrc99A (Pharmacia, Piscataway, N.J.), as shown in Table 12.

TABLE 12

The Expression Plasmids used for Expression of *P. aeruginosa* Operon and its Components

| Expression Vector | Selection Marker | Gene |
|---|---|---|
| pD100-phhabc | Cm | Full operon |
| pD100-phha | Cm | Phh A |
| pD100-phhbc | Cm | Phh B/phh C |
| pTrc-phha | Amp | Phh A |
| pTrc-phhb | Amp | Phh B |
| pTrc-phhc | Amp | Phh C |
| pTrc-phhbc | Amp | Phh B/phh C |
| pKSM-phha | Kan | Phh A |
| pKSM-phhb | Kan | Phh B |
| pKSM-phhc | Kan | Phh C |

The *E. coli* strains were transformed electroporationally with the expression vectors were grown at 37° C. in LB medium containing either 25 μg/ml of chlorophenicol for pD100 expression vectors or 100 μg/ml of ampicillin for both pKK223-3 and pTrc 19A expression vectors (Table 12) in the absence or presence of isopropyl-beta-D-thiogalactoside (IPTG).

EXAMPLE 11

Growth of *E. coli* AT271 Tyr-Auxotrophic Strain Following its Transformation with *C. violaceum* PAH and the Various Components of the *P. aeruginosa* PAH Operon Agar plates containing M9 medium plus glucose were prepared. The tyrosine auxotrophic AT271 strain is incapable of growing on this plate in the absence of tyrosine (see Control-1). When a filter disc containing 1.0 mM tyrosine is added to the plate, growth is observed around the disc indicating the dependency of the organism to the presence of tyrosine (see Control-2). The AT271 recombinant strains used in this study included strains containing PhhA, PhhB, PhhC, PhhBC, PhhABC, PAH and PAH/PhhB/PhhC. The tyrosine disc was placed in the middle of each of the plates for these recombinants. For the strains containing PhhA, PhhB, PhhC, and PhhBC growth appeard only around the tyrosine disc indicating that these strains could not synthesize tyrosine and were still dependent on the external supply of this compound for growth. However, with recombinant strains containing PhhABC, PAH and PAH/PhhB/PhhC growth occurred on the entire plate attesting to the ability of the organism to synthesize the required tyrosine for its growth and the lack of need for the external tyrosine containing disc.

EXAMPLE 12

The Effect of Iron on Growth and Tyrosine Production by Transformants of Phenylalanine Overproducing E. coli Containing the PAH Gene In order to examine the effect of iron on the activity of PAH and therefore production of tyrosine, E. coli strains containing the PAH gene of the C. violaceum (PAH) [SEQ ID NO:1] and the PhhA component of the Pseudomonas PAH operon were grown in the M9 medium with glucose with and without addition of either $FeSO_4$ or $Fe(NH_4)_2(SO_4)_2$ (1.0 M final conc.). Samples were taken at 2.0, 6.0, 16.0, and 22 hours. The results are shown in the Table 13. Based on the results obtained, it was concluded that addition of neither of the two iron sources had any significant positive effect on the level of the tyrosine produced.

TABLE 13

Tyrosine Production of Phenylalanine Overproducing Strain (ATCC31884) Transformed with PAH from C. violaceum in the Presence and Absence of $Fe^{+2}$

| Time (hour) | Presence of $Fe^{+2}$ | Absence of $Fe^{+2}$ |
| --- | --- | --- |
| 0 | 0 | 0 |
| 6 | 132.68 | 146.76 |
| 16 | 173.79 | 171.77 |
| 22 | 212.99 | 208.58 |

EXAMPLE 13

Determination of the Levels of Phenylalanine Produced by Various Phenylalanine Overproducing E. coli Strains The phenylalanine overproducing E. coli strains (ATCC 31882, 31883, 31884) in which inhibition of the enzyme DAHP synthase by phenylalanine, or tryptophan is removed and inhibition of the enzyme chorismate mutase P-prephenate dehydratase by phenyalanine is removed and in which enhanced levels of production of the enzymes DAHP synthase, chorismate mutase P-prephenate dehydratase and shikimate kinase are achieved (Tribe, D. E. Novel microorganism and method, U.S. Pat. No. 4,681,852, 1987), were tested for their ability to produce phenylalanine when grown in the M9 medium containing glucose. Strain ATCC 31884 produced the highest level of phenylalanine (870.54M) as shown in Table 14.

TABLE 14

Production of Phenylalanine by Phenylalanine Overproducing Strain (ATCC 31882, 31883 and 31884)

| E. coli Strain | Phenylalanine (µM) |
| --- | --- |
| Control | 0 |
| 31882 | 650.11 |
| 31883 | 418.23 |
| 31884 | 870.54 |

EXAMPLE 14

Production of Cinnamate and Para-hydroxycinnamate by the Phenylalanine Overproducing E. coli Strains (ATCC 31884)

Experiments were performed in order to test the ability of strain ATCC 31884 transformed with the native PAL/TAL enzyme from Rhodotorula graminis to produce cinnamate and PHCA. The E coli strain (DH5α) was used as the control and also a test strain following incorporation of the PAL/TAL enzyme. The third strain was the phenylalanine overproducer E. coli strains ATCC 31884 with the native PAL/TAL enzyme. All strains were grown in the M9 plus glucose medium and samples were taken (after 18 hrs) and prepared for HPLC analysis as described before. The results are shown in Table 15. It was interesting to note that no significant differences were observed between the levels of PHCA and cinnamate produced by strain DH5α containing the native PAL/TAL. However, much higher levels of cinnamate (~750 M) were produced by the phenylalanine over-producing strain ATCC 31884 plus PAL/TAL compared to PHCA (175 M). These results provide yet another evidence for the higher level of PAL activity compared with TAL activity in the native PAL/TAL enzyme of Rhodotorula graminis.

TABLE 15

Production of PHCA and Cinnamate by PAL Transformants

| Transformant | PHCA (µM) | Cinnamate (µM) |
| --- | --- | --- |
| DH5alph (Control) | 0 | 0 |
| DH5α + PAL/TAL | 285.23 | 375.33 |
| 31884 + PAL/TAL | 175.55 | 749.74 |

---

What is claimed is:

1. A method for the production of tyrosine comprising:
a) providing a recombinant microorganism comprising at least one nucleic acid fragment encoding a phenylalanine hydroxylase polypeptide,
  wherein said at least one nucleic acid fragment encoding a phenylalanine hydroxylase polypeptide is selected from the group consisting of:
  1) an isolated nucleic acid fragment isolated from Pseudomonas genomic DNA by a polymerase chain reaction protocol using any two primers selected from the group consisting of SEQ ID NOS:7-16 and the following amplification conditions:
     i) 1.0 mg of the genomic DNA template,
     ii) 2.5 units of Taq DNA polymerase in 10 mM Tris-HCl,
     iii) 0.2 mM each of the four dNTPs, 50 mM KCl, 1.5 mM MgCl2, and 0.01% bovine serum albumin, and
     iv) thermalcycling reaction of 94° C., 0.5 min; 55° C., 0.5 min and 72° C., 2.0 mm, and
  2) an isolated nucleic acid fragment encoding the polypeptide as set forth in SEQ ID NO:2; and
b) growing said recombinant microorganism in the presence of a fermentable carbon substrate whereby tyrosine is produced.

2. A method according to claim 1 wherein said fermentable carbon substrate is selected from the group consisting of monosaccharides, oligosaccharides, polysaccharides, carbon dioxide, methanol, formaldehyde, formate, and carbon-containing amines.

3. A method according to claim 1 wherein said fermentable carbon substrate is glucose.

4. A method according to claim 1 wherein said recombinant organism is selected from the group consisting of bacteria, yeasts, filamentous fungi, and algae.

5. A method according to claim 4 wherein said recombinant organism is selected from the group consisting of *Escherichia, Salmonella Bacillus, Acinetobacter, Streptomyces, Methylobacter, Rhodococcus, Pseudomonas; Cyanobacteria, Rhodobacter, Synechocystis, Saccharomyces, Zygosaccharomyces, Kluyveromyces, Candida, Hansenula, Debaryomyces, Mucor, Pichia, Torulopsis, Aspergillus* and *Arthrobotrys*.

* * * * *